US010612065B2

(12) United States Patent
Anderson et al.

(10) Patent No.: US 10,612,065 B2
(45) Date of Patent: Apr. 7, 2020

(54) HEAT TREATMENT TO PRODUCE GLYCOSIDES

(71) Applicant: CARGILL, INCORPORATED, Wayzata, MN (US)

(72) Inventors: James C. Anderson, Eden Prairie, MN (US); Robert J. Brower, III, Clayton, OH (US); Ting Liu Carlson, Marietta, SC (US); Belit Flores, Minneapolis, MN (US); Dan S. Gaspard, Victoria, MN (US); Kristopher T. Mortenson, Burnsville, MN (US); Richard Nygaard, Longmont, CO (US); Nicole Paulson, Buffalo, MN (US); Maribeth Rasmussen, Crystal, MN (US)

(73) Assignee: Cargill, Incorporated, Wayzata, MN (US)

( * ) Notice: Subject to any disclaimer, the term of this patent is extended or adjusted under 35 U.S.C. 154(b) by 7 days.

(21) Appl. No.: 15/578,154

(22) PCT Filed: May 27, 2016

(86) PCT No.: PCT/US2016/034781
§ 371 (c)(1),
(2) Date: Nov. 29, 2017

(87) PCT Pub. No.: WO2016/196345
PCT Pub. Date: Dec. 8, 2016

(65) Prior Publication Data
US 2018/0163244 A1   Jun. 14, 2018

Related U.S. Application Data

(60) Provisional application No. 62/168,142, filed on May 29, 2015.

(51) Int. Cl.
*C12P 19/56* (2006.01)
*A23L 2/60* (2006.01)
*A61K 31/704* (2006.01)
*C12N 15/81* (2006.01)

(52) U.S. Cl.
CPC ............... *C12P 19/56* (2013.01); *A23L 2/60* (2013.01); *A61K 31/704* (2013.01); *C12N 15/81* (2013.01); *C12N 2523/00* (2013.01)

(58) Field of Classification Search
CPC ........................................................ C12N 1/20
USPC ...................................................... 435/252.3
See application file for complete search history.

(56) References Cited

U.S. PATENT DOCUMENTS

2002/0164700 A1   11/2002   Andersen et al.
2006/0083838 A1*   4/2006   Jackson ................... C07H 1/00
                                                                426/548
2006/0134742 A1   6/2006   Brazeau et al.
2010/0184133 A1   7/2010   Norgaard et al.
2011/0081697 A1   4/2011   Liu et al.
2011/0189717 A1   8/2011   Ajikumar et al.
2012/0164678 A1*   6/2012   Stephanopoulos ...... A01H 5/00
                                                                435/29
2012/0165562 A1   6/2012   Hattendorf et al.
2013/0071339 A1   3/2013   Markosyan et al.
2013/0171328 A1   7/2013   Kishore et al.
2014/0329281 A1   11/2014   Houghton-Larsen et al.
2014/0357588 A1   12/2014   Markosyan et al.
2015/0031868 A1   1/2015   Lehmann et al.
2015/0037462 A1   2/2015   Markosyan et al.
2016/0348192 A1   12/2016   Tilloy et al.
2018/0148750 A1   5/2018   Anderson et al.
2018/0155751 A1   6/2018   Anderson et al.
2018/0230504 A1   8/2018   Anderson et al.

FOREIGN PATENT DOCUMENTS

| EP | 1305440 B1 | 6/2011 |
|---|---|---|
| WO | WO0125467 | 4/2001 |
| WO | WO2009140394 | 11/2009 |
| WO | WO2011153378 | 12/2011 |
| WO | WO2013022989 | 2/2013 |
| WO | WO2013096420 | 6/2013 |
| WO | WO2013110673 | 8/2013 |
| WO | WO2014122227 | 8/2014 |
| WO | WO2014122328 | 8/2014 |
| WO | WO2014145521 | 9/2014 |
| WO | WO2014191581 | 12/2014 |
| WO | WO2014193888 | 12/2014 |
| WO | WO2014193934 | 12/2014 |
| WO | WO2015011209 | 1/2015 |
| WO | 2015014959 A1 | 2/2015 |
| WO | WO2015014969 | 2/2015 |
| WO | WO2016196321 | 12/2016 |
| WO | WO2016196368 | 12/2016 |
| WO | WO2017024313 | 2/2017 |

OTHER PUBLICATIONS

International Search Report of PCT/US2016/034781 dated Aug. 29, 2016 (4 pgs.).
Chisti, Y. "Fermentation (Industrial): Basic Considerations" in: "Encyclopedia of Food Microbiology" (1999 ed.), pp. 663-674 (1999).
International Preliminary Report on Patentability from then International Search Authority for International Application No. PCT/US2016/034781; dated Aug. 3, 2016, pp. 1-9.
Kizer et al., "Application of functional genomics to pathway optimization for increased isoprenoid production," Appl Environ Microbiol.; 74(10):3229-41 (2008).
Prather et al., "De novo biosynthetic pathways: rational design of microbial chemical factories," Curr Opin Biotechnol. 19(5):468-74 (2008).
"Nomenclature committee of the international union of biochemistry and molecular biology (NC-IUBMB), Enzyme Supplement 5 (1999)," Eur J Biochem. 264(2):610-50, (1999).

(Continued)

Primary Examiner — Tekchand Saidha
(74) Attorney, Agent, or Firm — McDonnell Boehnen Hulbert & Berghoff LLP

(57) ABSTRACT

Disclosed are methods of releasing or enriching for steviol glycosides produced by yeast. The disclosed methods enhance or improve the release or enrichment of the steviol glycosides.

15 Claims, 5 Drawing Sheets

Specification includes a Sequence Listing.

(56) References Cited

OTHER PUBLICATIONS

Anderlei et al., "Device for sterile online measurement of the oxygen transfer rate in shaking flasks," Biochemical Engineering Journal 3478:1-6, (2000).

Barrett, "Nomenclature Committee of the International Union of Biochemistry and Molecular Biology (NC-IUBMB). Enzyme nomenclature. Recommendations 1992. Supplement 2: corrections and additions (1994)," Eur. J. Biochem., 232:1-6, (1995).

Barrett, "Nomenclature Committee of the International Union of Biochemistry and Molecular Biology (NC-IUBMB). Enzyme nomenclature. Recommendations 1992. Supplement 3: corrections and additions (1995)," Eur J Biochem. 237 (1):1-5 (1996).

Barrett, "Nomenclature Committee of the International Union of Biochemistry and Molecular Biology (NC-IUBMB). Enzyme Nomenclature. Recommendations 1992. Supplement 4: corrections and additions (1997)," Eur J Biochem. 250(1):1-6 (1997).

Chen et al., "The glucose RQ-feedback control leading to improved erythromycin production by a recombinant strain Saccharopolyspora erythraea ZL1004 and its scale-up to 372-m(3) fermenter," Bioprocess Biosyst Eng. 38(1):105-12 (2015).

Jasmin, et al., "The yield of experimental yeast populations declines during selection," Proc Biol Sci. 2012. vol. 279 (1746): p. 4382-8 (2012).

Jules, et al., "Two Distinct Pathways for Trehalose Assimilation in the Yeast *Saccaromyces cerevisiae*," Appl Environ C Microbiol., vol. 70(5), p. 2771-2778 (2004).

Li et al., "Phylogenetic analysis of the UDP-glycosyltransferase multigene family of *Arabidopsis thaliana*," J Biol Chem. 276(6):4338-43 (2001).

Lynd et al., "Microbial cellulose utilization: fundamentals and biotechnology," Microbial. Mol. Biol. Rev., 66:506-577 (2002).

Ohta et al., "Characterization of Novel Steviol Glycosides from leaves of Stevia rebaudiana Morita", Journal of Applied Glycoscience, The Japanese Society of Applied Glycoscience, Aug. 17, 2010, Issue 57, pp. 199-209.

Prakash et al., "Isolation, characterization and sensory evaluation of a Hexa beta-D-glucopyranosyl diterpene from Stevia rebaudiana," Nat Prod Commun. 8(11):1523-6 (2013).

Prakash et al., "Catalytic hydrogenation of the sweet principles of Stevia rebaudiana, Rebaudioside B, Rebaudioside C, and Rebaudioside D and sensory evaluation of their reduced derivatives," Int J Mol Sci. 13(11):15126-36 (2012).

Tipton, "Nomenclature Committee of the International Union of Biochemistry and Molecular Biology (NC-IUBMB). Enzyme nomenclature. Recommendations 1992. Supplement: corrections and additions," Eur J Biochem., 223(1):1-5 (1994).

Verduyn, C. et al., "Effect of benzoic acid on metabolic fluxes in yeasts: a continuous-culture study on the regulation of respiration and alcoholic fermentation," Yeast 8, 501-517 (1992).

* cited by examiner

HEAT TREATMENT TO PRODUCE GLYCOSIDES

CROSS-REFERENCE TO RELATED APPLICATIONS

This application is a national phase application of PCT/US2016/034781, filed May 27, 2016, and entitled HEAT TREATMENT TO PRODUCE GLYCOSIDES, which claims the benefit of U.S. Provisional Patent Application No. 62/168,142, filed May 29, 2015, and entitled HEAT TREATMENT TO PRODUCE GLYCOSIDES, each of which is hereby incorporated by reference in its entirety.

REFERENCE TO SEQUENCE LISTING

This application contains references to amino acid sequences and/or nucleic acid sequences which have been submitted concurrently herewith as an ASCII text file entitled "CAR0211WO_Sequence_Listing.txt," created on May 27, 2016, and having a size of 92 kilobytes. The sequence listing is hereby incorporated by reference in its entirety pursuant to 37 C.F.R. § 1.52(e)(5).

BACKGROUND

Sugars, such as sucrose, fructose and glucose, are utilized to provide a pleasant taste to beverages, foods, pharmaceuticals, oral hygienic and cosmetic products. Sucrose, in particular, imparts a taste preferred by most consumers. Although sucrose provides superior sweetness characteristics, it is caloric. Non-caloric or lower caloric sweeteners have been introduced to satisfy consumer demand. Consumers also desire that these sweeteners have favorable taste characteristics.

*Stevia* is a genus of about 240 species of herbs and shrubs in the sunflower family (Asteraceae), native to subtropical and tropical regions and from western North America to South America. The species *Stevia rebaudiana*, commonly known as sweetleaf, sweet leaf, sugarleaf, or simply *stevia*, is widely grown for its sweet leaves. *Stevia*-based sweeteners may be obtained by extracting one or more sweet compounds from the leaves. Many of these compounds are glycosides of steviol, a diterpene compound. These diterpene glycosides are about 150 to 450 times sweeter than sugar. Steviol glycosides differ from each other by sweetness power as well as other sensory features contributing to taste quality such as bitterness, lingering aftertaste and the like. See Kinghorn, A. D., *Stevia*: The genus *Stevia*, Taylor & Francis, London (2002).

Examples of steviol glycosides are described in PCT International Patent Application Publication No. WO 2013/096420 (see, e.g., listing in FIG. 1); and in Ohta et. al., "*Characterization of Novel Steviol Glycosides from Leaves of Stevia rebaudiana Morita*," J. Appl. Glycosi., 57, 199-209 (2010) (see, e.g., Table 4 at p. 204). Structurally, the diterpene glycosides are characterized by a single base, steviol, and differ by the presence of carbohydrate residues at positions C13 and C19, as presented in FIGS. 2a-2k of WO 20013/096420.

Typically, on a dry weight basis, the four major steviol glycosides found in the leaves of *Stevia* are dulcoside A (0.3%), rebaudioside C (0.6-1.0%), rebaudioside A (3.8%) and stevioside (9.1%). Other glycosides identified in *Stevia* extract include one or more of rebaudioside B, D, E, F, G, H, I, J, K, L, M, N, O, steviolbioside and rubusoside.

While the major steviol glycoside, rebaudioside A, is commonly used as sweetener in beverage applications it has off-taste issues. More recently, there has been focus on certain minor steviol glycosides which have better taste properties. For example, rebaudioside M has higher sweetness intensity and is more potent than other steviol glycosides (e.g., see Prakash, L, et al. (2013) Nat. Prod. Commun., 8: 1523-1526, and WO 2013/096420). Rebaudioside D tastes about 200-220 times sweeter than sucrose and in a sensory evaluation had a slow onset of sweetness and was very clean, namely sweeter overall than sucrose, less sweet lingering aftertaste compared to sucrose (e.g., see Prakash, I., et al. (2012) Int. J. Mol. Sci., 13:15126-15136).

Recombinant DNA technology has made it possible, and commercially viable, to produce desired steviol glycosides using a wide variety of host cells such as yeast. Recovery of intracellularly expressed products from within the host cells, however, is fraught with difficulties because of the necessity of rupturing or hydrolyzing the tough yeast cell wall. The choice of cell wall disruption can also affect the downstream processing of the recovered product and its subsequent purification from yeast cells or fermentation broths thereby affecting the efficiency and cost effectiveness of the process.

SUMMARY

Disclosed is a method to efficiently recover desired steviol glycosides produced by recombinant yeast technology in a cost effective manner.

Disclosed, in one aspect of the invention, is a method of releasing steviol glycosides from a host cell, comprising heating a fermentation medium comprising steviol glycoside producing engineered host cells to a temperature in the range from 50° C. to 95° C. for 5 minutes to 48 hours to release one or more steviol glycosides from the engineered host cells into the fermentation medium.

Disclosed in another aspect of the invention is a method of releasing steviol glycosides from a host cell, comprising the steps of:
  a) providing a fermentation medium comprising a host cell engineered to produce one or more steviol glycosides; and
  b) releasing the one or more steviol glycosides from the engineered host cell by heating the composition to a temperature in the range from 50° C. to 95° C. for 5 minutes to 48 hours,
    wherein the one or more steviol glycosides are released from an intracellular portion of the host cell into an extracellular portion of the fermentation medium.

Disclosed in yet another aspect of the invention is a method of releasing steviol glycosides from a composition, the method comprising the step of heating the composition to a temperature in the range from 50° C. to 95° C. for 5 minutes to 48 hours to release the steviol glycosides from engineered host cells in the composition.

Disclosed, in another aspect of the invention, is a method of releasing steviol glycosides, the method comprising the steps of:
  a) providing a composition comprising an engineered host cell to produce one or more steviol glycosides; and
  b) releasing the one or more steviol glycosides from the engineered host cell by heating the composition to a temperature in the range from 50° C. to 95° C. for 5 minutes to 48 hours.

Disclosed, in another aspect of the invention, is a composition comprising an engineered host cell to produce one or more steviol glycosides, and one or more steviol glycosides that are released from the engineered host cell by heating the composition to a temperature in the range from 50° C. to 95° C. for 5 minutes to 48 hours.

Such methods result in releasing the glycosides into the composition while minimizing cell lysis.

DETAILED DESCRIPTION

Figure 1:
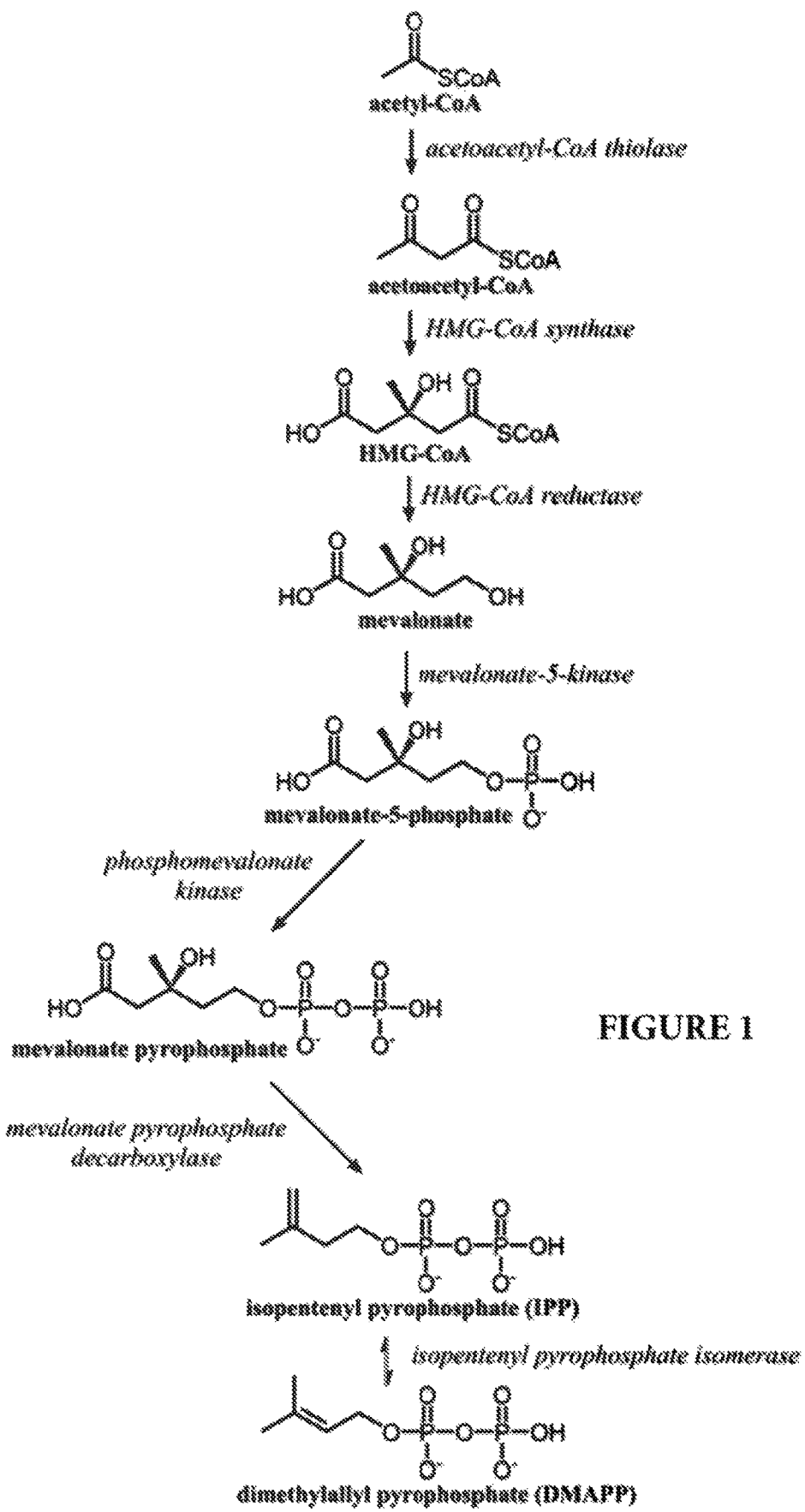
FIG. 1 shows a representative mevalonate pathway.

Embodiments of the disclosure described herein are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated. All publications and patents mentioned here are hereby incorporated by reference in their entirety. The publications and patents disclosed here are provided solely for their disclosure.

Host cells such as yeast and fungus can be engineered for the synthesis of steviol glycosides. During fermentation only a fraction of the glycosides produced by the host cell may be released from within the cells into the fermentation media. To increase the glycoside amount released from the host cell such as yeast, mechanical and chemical disruption methods may be used. Mechanical disruption, namely the breaking of the cell, releases the intracellular components into the surrounding medium. The result is a complex mixture of not only the desired recombinant product but also other products such as protein, nucleic acids, cellular metabolites, cell fragments, complicating the recovery of the desired product. Chemical methods entail chemically altering or making permeable the cell membrane and/or wall structure to allow diffusion of the product from within the cell. Chemical treatments, however, have to be compatible with the organism and the release of the desired product.

Disclosed are methods of efficiently recovering steviol glycosides after fermentation using heat treatments. Heat applied for a given time period and temperature to a fermentation broth or fermentation medium that includes host cells (e.g. yeast and fungus). The host cells can produce the desired steviol glycosides. When the fermentation medium containing the host cells are heated, the desired glycosides can be released from the host cells with minimal lysis of the cells thereby enriching the fermentation media or composition for the desired glycoside.

In some embodiments, the disclosed methods use engineered yeast capable of producing steviol glycosides. An engineered yeast capable of producing steviol glycosides can include one or more exogenous nucleic acids that encode enzyme(s) that promote formation of one or more steviol glycosides in the cell.

As used herein, the term "steviol glycoside(s)" refers to glycosides of steviol. Exemplary steviol glycoside, include, but are not limited to, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, stevioside, steviolbioside, dulcoside A, and/or rubusoside. Engineered yeast can produce steviol glycosides that are naturally found ("naturally occurring") or ones that are not found in nature (non-naturally occurring). As used herein, the term "total steviol glycosides" (TSG) is calculated as the sum of the content of all steviol glycosides in a composition on a dry (anydrous) basis.

Structurally, steviol glycosides have a central molecular moiety, which is a single steviol base, and glucopyranosyl residues, or other sugar residuals attached to the $C_{13}$ and $C_{19}$ atoms of the steviol base, according to the atom numbering on the base shown below. That is, glucopyranosyl residues represent groups $R_1$ and $R_2$ in the following formula:

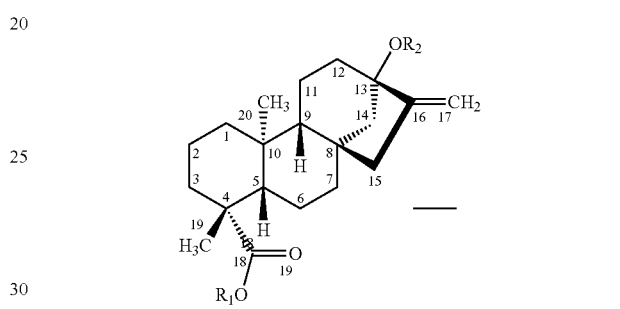

Table A below shows the certain steviol glycosides and the corresponding $R_1$ and $R_2$ groups:

TABLE A

| Compound name | $R_1$ (C-19) | $R_2$ (C-13) |
|---|---|---|
| Steviol | H | H |
| Stevioside | β-Glu | β-Glu-β-Glu (2->1) |
| Rebaudioside A | β-Glu | β-Glu-β-Glu (2->1)<br>\|<br>β-Glu (3->1) |
| Rebaudioside B | H | β-Glu-β-Glu (2->1)<br>\|<br>β-Glu (3->1) |
| Rebaudioside C | β-Glu | β-Glu-α-Rha (2->1)<br>\|<br>β-Glu (3->1) |
| Rebaudioside D | β-Glu-β-Glu (2->1) | β-Glu-β-Glu (2->1)<br>\|<br>β-Glu (3->1) |
| Rebaudioside E | β-Glu-β-Glu (2->1) | β-Glu-β-Glu (2->1) |
| Rebaudioside G | β-Glu | β-Glu-β-Glu (3->1) |
| Rebaudioside M | β-Glu-β-Glu (2->1)<br>\|<br>β-Glu (3->1) | β-Glu-β-Glu (2->1)<br>\|<br>β-Glu (3->1) |
| Rebaudioside N | β-Glu-α-Rha (2->1)<br>\|<br>β-Glu (3->1) | β-Glu-β-Glu (2->1)<br>\|<br>β-Glu (3->1) |

TABLE A-continued

| Compound name | $R_1$ (C-19) | $R_2$ (C-13) |
|---|---|---|
| Rebaudioside O | β-Glu-α-Rha (2->1)-β-Glu (3->1)<br>\|<br>β-Glu (3->1) | β-Glu-β-Glu (2->1)<br>\|<br>β-Glu (3->1) |

Glu: glucose
Rha: rhamnose

The disclosed steviol glycosides may be produced in a fermentation process. The fermentation process can use a genetically modified organism that is engineered for the production of one or more steviol glycosides, such as rebaudioside A (Reb A), rebaudioside M (Reb M) and/or rebaudioside D (Reb D). Production of steviol glycosides can be carried out using an engineered microbial strain having a set of enzymes that provide a pathway for the synthesis of steviol glycosides.

Various yeast or fungal host cells can be engineered to provide a pathway to one or more steviol glycosides. Such cells can be transformed with one or more DNA construct encoding enzymes for steviol glycoside synthesis. Exemplary yeast and fungus that can be used for hosts for exogenous DNA constructs encoding steviol glycoside pathway enzymes, include, but are not limited to the genus of, *Candida*, *Pichia* (*Hansenula*), *Kloeckera* (*Hanseniaspora*), *Kluyveromyces*, *Rhodotorula*, *Torulopsis*, *Zygosaccharomyces*, *Saccharomycete*, *Yarrowia*, and *Saccharomyces*. Exemplary species include *Candida albicans*, *Pichia pastoris*, *Saccharomyces cerevisiae*, and *Schizosaccharomyces pombe*. Further, host cells can also include genetic modifications other than those of the steviol glycoside pathway that may provide improved performance during fermentation.

An "engineered host cell" refers to yeast and fungal cells having at least one exogenous DNA sequence that is introduced into the cell, either integrated into the cell's genome or present on an extrachromosomal construct, such as a plasmid in bacteria or episomes. While the specification may describe yeast cells in detail, it should be understood that the present disclosure may also be adapted to fungal cells.

The term "exogenous" refers to a molecule, such as a nucleic acid, or an activity, such as an enzyme activity. The exogenous molecule is introduced into the host yeast or fungus. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. Generally, the genome of an engineered yeast or fungus is augmented through the stable introduction of one or more recombinant genes. An exogenous nucleic acid can encode an enzyme, or portion thereof, that is either homologous or heterologous to the host organism. An exogenous nucleic acid can be in the form of a "recombinant gene or DNA construct" referring to a nucleic acid that is in one or more ways manipulated through molecular techniques to be in a form that does not naturally exist. The term "non-natural" may be used to characterize a molecule, such as a nucleic acid or protein, or an organism that does not naturally exist in nature.

The term "heterologous" (e.g., "non-native") refers to a molecule or activity that is from a source that is different than the referenced molecule or organism. Accordingly, a gene or protein that is heterologous to a referenced organism is a gene or protein not found in that organism. In the context of the disclosure, a "heterologous glycosyltransferase" refers to a glycosyltransferase polypeptide that is different from any glycosyltransferase polypeptide that may be native to the host organism. For example, a specific glycosyltransferase gene found in a first species and exogenously introduced into a host yeast or fungal organism that is different than the first species is "heterologous" to the host yeast or fungal organism.

The engineered yeast or fungus can use an auxotrophic marker suitable for selecting for a transformant. The host cell can include modifications (e.g. deletions) in one or more genes that control auxotrophies, such as LYS2, LEU2, HIS3, URA3, URA5, and TRP1. Using a host cell having a desired genetic background for introduction of one or more exogenous genes, one or more gene construct(s) is introduced into a cell to integrate into the genome, or to be stably maintained and allow for expression. Methods for introducing a gene construct into a host cell include transformation, transduction, transfection, co-transfection, electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the steviol pathway genes can be confirmed using methods well known in the art. Such methods include, for example, nucleic acid analysis such as Northern blots or polymerase chain reaction (PCR) amplification, or immunoblotting for expression of gene products, or other suitable analytical methods to test the expression of the introduced nucleic acid sequences or their corresponding gene product. It is understood by those skilled in the art that the exogenous nucleic acid is expressed in an amount sufficient to produce the desired product, and it is further understood that expression levels can be optimized to obtain sufficient expression using methods well known in the art and as disclosed herein.

The terpenoid compounds, isopentenyl diphosphate (IPP) and dimethylallyl diphosphate (DMAPP), can serve as chemical precursors to steviol glycosides in an engineered host cell (e.g. yeast). Some organisms, including plants, insect, and some microbial species, have a mevalonate (MVA) pathway that converts acetyl-CoA through a series of chemical intermediates to IPP and DMAPP. Some organisms produce IPP and DMAPP through the non-mevalonate pathway (also known as the methyl D-erythritol 4-phosphate or MEP pathway) starting with glyceraldehyde-3-phosphate (G3P) and pyruvate (PYR).

The yeast *Saccharomyces cerevisiae* naturally expresses genes of the mevalonate pathway. Mevalonate pathway genes include: (a1) acetoacetyl CoA thiolase (EC 2.3.1.9), (b1) 3-hydroxy-3-methylglutaryl-coenzyme A (HMG-CoA) synthase (EC 4.1.3.5); (c1) HMG-CoA reductase (EC 1.1.1.34); (d1) mevalonate kinase (EC 2.7.1.36); (e1) phosphomevalonate kinase (EC 2.7.4.2); and (f1) mevalonate diphosphate decarboxylase (EC 4.1.1.33). Mevalonate pathway enzymes convert acetyl-CoA to IPP as follows: acetyl-CoA→acetoacetyl-CoA→3-hydroxy-3-methylglutaryl-CoA mevalonate→mevalonate-5-phosphate→mevalonate-5-pyrophosphate→IPP. See also FIG. 1

In some embodiments, the engineered yeast can include one or more modifications to increase the flux from acetyl-CoA to IPP and/or DMAPP, thereby providing an increased pool of IPP and/or DMAPP for use in a pathway to steviol. The modifications can include, for example, increasing expression or activity of one or more mevalonate pathway enzymes (a1)-(f1), such as by placing a nucleic acid encoding an enzyme that is homologous or heterologous to the yeast cell under the control of a promoter that provides increased expression, using multiple copies of the nucleic acid, and/or using a heterologous enzyme, a variant enzyme (e.g., including one or more amino acid substitutions), or a variant heterologous enzyme that provides a higher level of enzymatic activity as compared to the native enzyme.

Alternatively, the non-mevalonate (MEP) pathway can be used to provide IPP and DMAPP as precursors to steviol glycoside production. The yeast *Saccharomyces cerevisiae* does not naturally express genes of the MEP pathway, but can optionally be engineered to provide MEP pathway genes. Theoretically, the MEP pathway is more energetically efficient generally because it loses less carbon as $CO_2$ as compared to the MVA pathway (MEP pathway: 1 $CO_2$/IPP; MVA pathway: 4 $CO_2$/IPP; sugar as carbon source).

Figure 2:
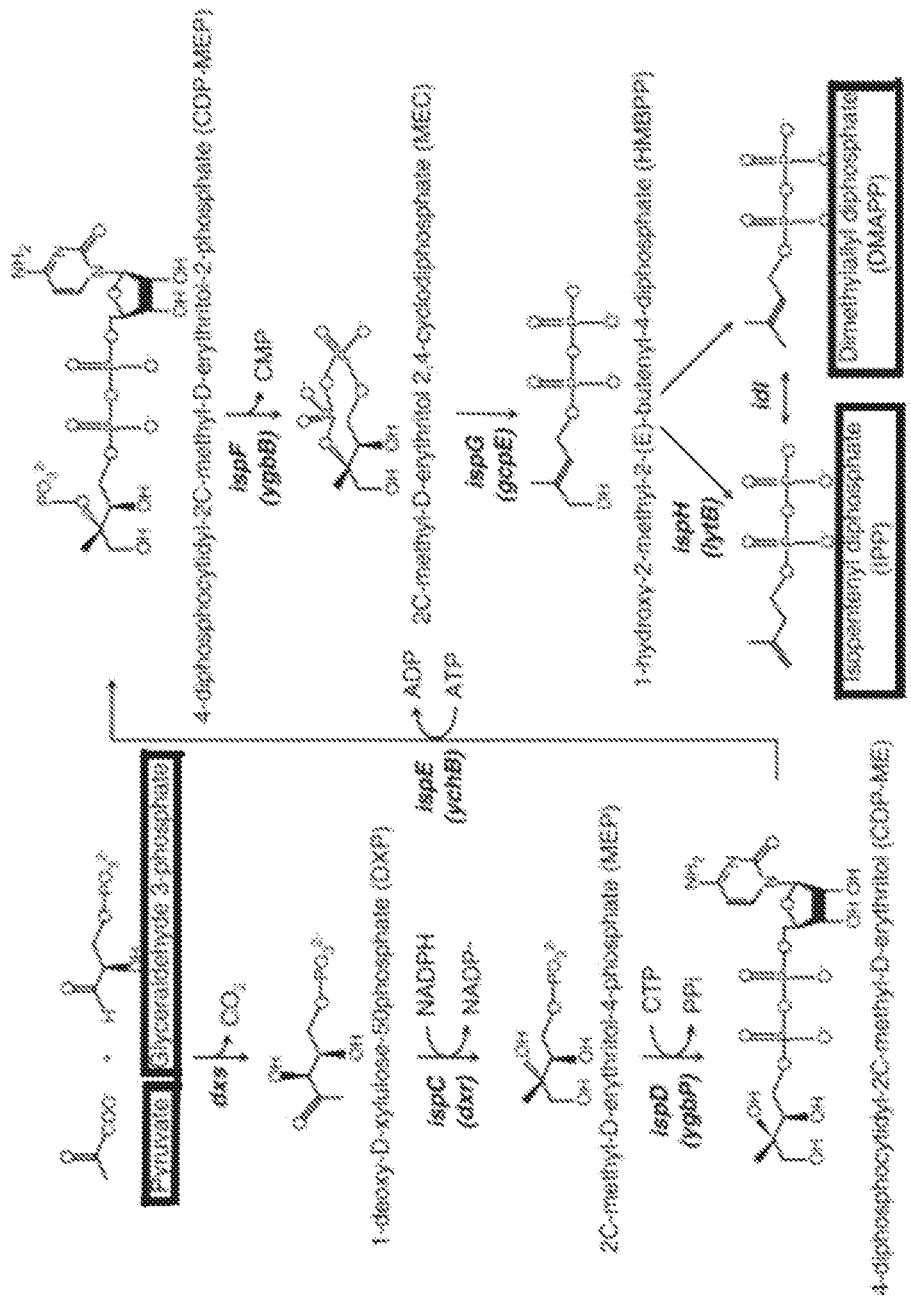
FIG. 2 shows a representative non-mevalonate pathway.

In particular, the non-mevalonate (MEP) pathway compounds, isopentenyl diphosphate (IPP), dimethylallyl diphosphate (DMAPP), are generated through a series of intermediates leading from glyceraldehydes-3-phosphate (G3P) and pyruvate (PYR), and a number of enzymes are responsible for this conversion. Enzymes involved in a biosynthetic pathway from G3P and PYR to IPP and DMAPP include (a2) 1-deoxy-D-xylulose-5-phosphate synthase (DXS), (b2) 1-Deoxy-D-xylulose-5-phosphate reductoisomerase (ispC)-, (c2) 4-diphosphocytidyl-2C-methyl-D-erythritol synthase (IspD), (d2) 4-diphosphocytidyl-2-C-methyl-D-erythritol kinase (IspE), (e2) 2C-Methyl-D-erythritol-2,4-cyclodiphosphate Synthase (IspF), (f2) 1-hydroxy-2-methyl-2-(E)-butenyl-4-diphosphate synthase (IspG), (g2) 4-hydroxy-3-methyl-2-(E)-butenyl-4-diphosphate reductase (IspH), and (h2) isopentenyl-diphosphate isomerase (IDI). See FIG. 2

The engineered yeast used to produce steviol glycosides by fermentation can have one or more genetic modifications to increase the flux from G3P and PYR to IPP and/or DMAPP, thereby providing an increased pool of IPP and/or DMAPP for use in a pathway to steviol. The modifications can include, for example, increasing expression or activity of one or more enzymes (a2)-(h2), such as by placing a nucleic acid encoding an enzyme that is heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a high levels of enzymatic activity.

Figure 3:
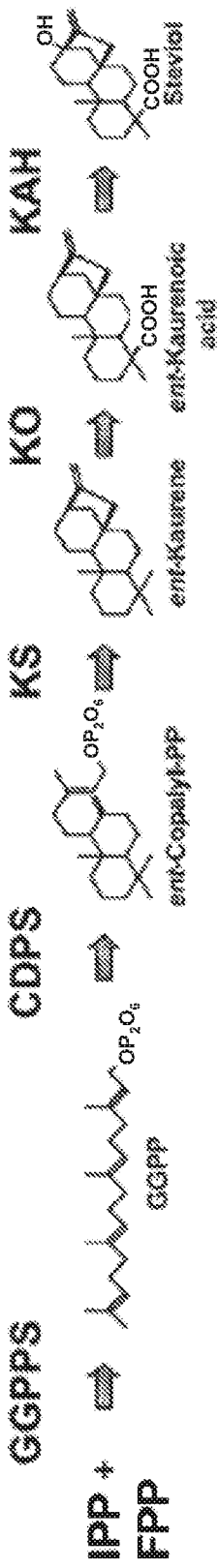
FIG. 3 shows a representative pathway for steviol production.

The engineered yeast used to produce steviol glycosides by fermentation can also include a pathway to convert IPP and/or DMAPP to steviol. For example, in some aspects the engineered yeast can include exogenous nucleic acids expressing the following enzymes: (a3) geranyl geranyl-diphosphate synthase (GGPPS), (b3) copalyl diphosphate synthase (CPS), (c3) kaurene synthase (KS), (d3) kaurene oxidase (KO), and (e3) kaurenoic acid 13-hydroxylase (KAH). Enzymes of the mevalonate pathway converts IPP and/or DMAPP to steviol as follows: IPP/DMAPP→geranyl geranyldiphosphate→copalyl diphosphate→kaurene→kaurenoic acid→steviol. (See FIG. 3) Exogenous nucleic acids encoding enzymes (a3)-(e3) that are heterologous to the yeast cell can be placed under the control of a promoter that provides increased expression, using multiple copies of the nucleic acid, and/or using a variant enzyme (e.g., one including one or more amino acid substitutions), or a variant heterologous enzyme that provides a high levels of enzymatic activity.

The methods of the disclosure for producing steviol glycoside(s) by fermentation can use engineered yeast including one or more steviol biosynthesis enzymes selected from the group of geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2 (E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The engineered yeast used to produce steviol glycosides by fermentation can have any pathway to convert steviol to a steviol glycoside. If more than one steviol glycoside pathway enzymes are present in the engineered yeast, the yeast may be able to produce different steviol glycosides. For example, the yeast may be able to produce two, three, four, five, six, seven, eight, nine, ten, or more than 10 different steviol glycoside species. In some embodiments, Reb A, Reb D and/or Reb M are produced by the engineered yeast cells.

Figure 4:
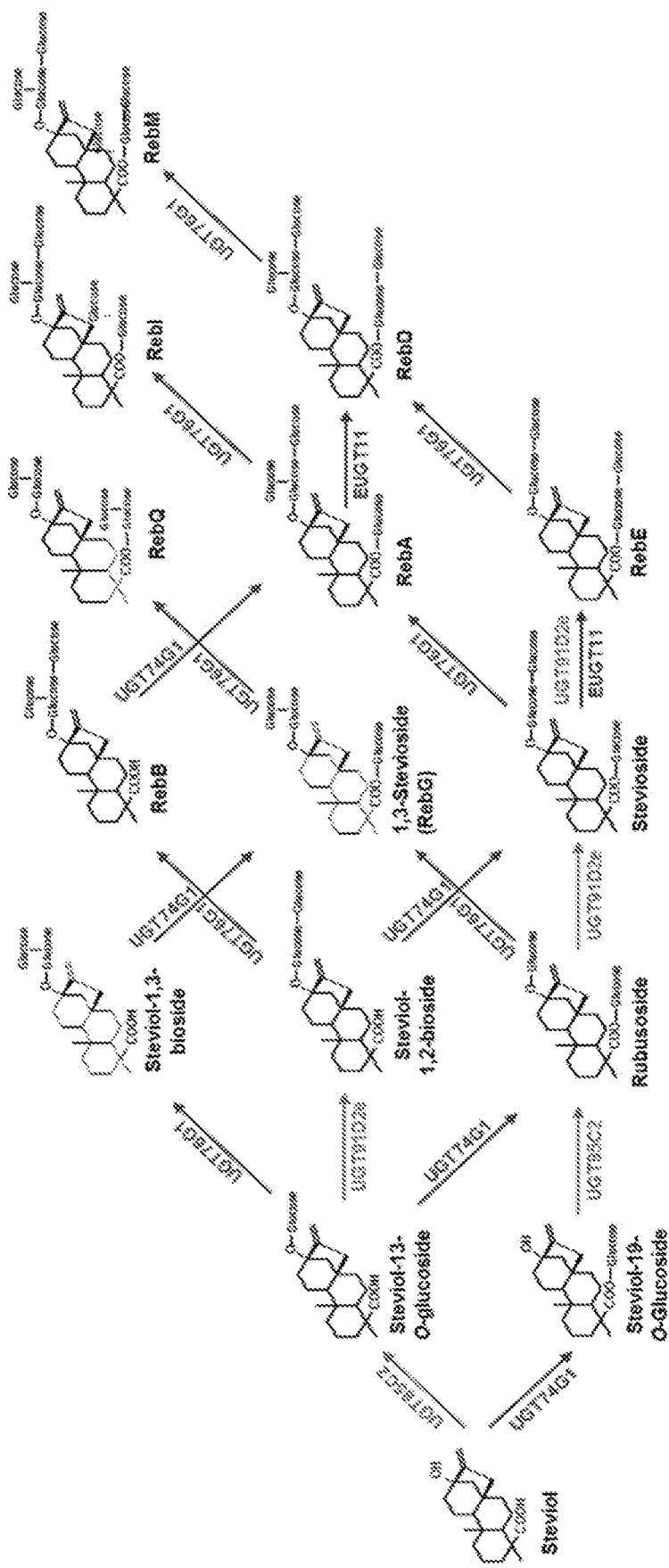
FIG. 4 shows representative pathways for the biosynthesis of steviol glycosides from steviol.

The steviol glycoside pathway can include one or more uridine diphosphate (UDP) glycosyltransferases (UGTs) that mediate the transfer of glycosyl residues from activated nucleotide sugars to acceptor molecules. In the case of a steviol glycoside pathway, a monosaccharide unit can be transferred to a hydroxyl or carboxyl moiety on a steviol or steviol glycoside molecule, or to a hydroxyl group on a glucose group that is attached to the steviol base. See FIG. 4. UGTs have been classified into families and subfamilies based on sequence homology. See Li et al, 2001, J. Biol. Chem. 276:4338-4343. A superfamily of over 100 genes encoding UGTs, each containing a 42 amino acid consensus sequence, has been identified in the model plant *Arabidopsis thaliana*, and genes encoding UGTs have also been identified in several other higher plant species.

Exemplary UDP-glucosyltransferase can be any UDP-glucosyltransferase capable of adding at least one glucose unit to the steviol and or steviol glycoside substrate to provide the desired steviol glycoside. In one embodiment, the engineered yeast can include one or more UDP-glucosyltransferase selected from group UGT74G1 (SEQ ID NO: 1), UGT85C2 (SEQ ID NO: 2), UGT76G1 (SEQ ID NO: 3), UGT91D2 (SEQ ID NO: 4), and also UGTs having substantial (e.g. >85%, >75%, >65%, >55%, >45% and >35%) identity to these polypeptides. An engineered yeast can include one or more exogenous nucleic acid molecule(s) that code for these UGTs.

The engineered yeast can also include one or more UGT and UDP-glucose recycling enzyme(s). An exemplary UDP-glucosyltransferase capable of adding at least one glucose unit to rubusoside to form stevioside is UGT91D2 (SEQ ID NO: 4). An exemplary UDP-glucosyltransferase capable of adding at least one glucose unit to stevioside to form rebaudioside A is UGT76G1 (SEQ ID NO: 3). An exemplary UDP-glucosyltransferase capable of adding at least one glucose unit to rebaudioside A to form rebaudioside D is UGT91D2 (SEQ ID NO: 4). An exemplary UDP-glucosyltransferase capable of adding at least one glucose unit to rebaudioside D to form rebaudioside M is UGT76G1 (SEQ ID NO: 3).

Exemplary publications that describe engineered microorganisms for steviol glycoside production include, for example, U.S. Patent Application Publication No. 2014/0357588, International Patent Application Publication Nos. WO 2014/193934, WO 2014/193888, and WO 2014/122227, which are hereby incorporated by reference in their entirety.

In one embodiment, an engineered yeast useful for the production of steviol glycosides expresses the following enzymes: geranylgeranyl diphosphate synthase (GGPPS), ent-copalyl diphosphate synthase (CDPS), kaurene oxidase (KO), kaurene synthase (KS); steviol synthase (KAH), cytochrome P450 reductase (CPR), UGT74G1, UGT76G1, UGT91D2, UGT85C2 and a EUGT11. WO2014/122227 describes an engineered yeast strain that express these enzymes. The UDP-glucosyltransferases can be a gene encoding a polypeptide for example, UGT74G1 (SEQ ID NO: 1), UGT85C2 (SEQ ID NO: 2), UGT76G1 (SEQ ID NO: 3), UGT91D2 (SEQ ID NO: 4), and a EUGT11 (SEQ ID NO: 13); these genes encode polypeptides capable of carrying out a number of reactions such as a) a gene encoding a polypeptide capable of beta 1,2 glucosylation of the CT of the 19-0 glucose of a steviol glycoside; (b) a gene encoding a polypeptide capable of beta 1,2 glucosylation of the CT of the 13-O-glucose of a steviol glycoside; (c) a gene encoding a polypeptide capable of beta 1,3 glucosylation of the C3' of the 19-O-glucose of a steviol glycoside; (d) a gene encoding a polypeptide capable of beta 1,3 glucosylation of the C3' of the 13-O-glucose of a steviol glycoside; (i) a gene encoding a polypeptide capable of glucosylation of the 13-OH of steviol or a steviol glycoside; (j) a gene encoding a polypeptide capable of glucosylation of the C-19 carboxyl of steviol or a steviol glycoside. For example, UGT85C2 carries out reaction (i); UGT74G1 carries out reaction (j); UGT91D2 carries out reactions (a; weakly), (b); UGT76G1 carries out reactions (c) and (d) EUGT11 carries out reactions (a), (b; less well).

In one embodiment the engineered host cell expresses one or more exogenous nucleic acid(s) encoding one or more of the following proteins heterologous to the host cell: GGPPS polypeptide, an enf-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91 d2 polypeptide, and a EUGT11 polypeptide.

In another embodiment, the engineered yeast expresses one or more exogenous nucleic acid(s) encoding one or more of the following proteins heterologous to the host cell: a GGPPS polypeptide, a truncated Zea mays CDPS polypeptide, an Arabidopsis thaliana KS polypeptide a Stevia rebaudiana KO polypeptide, an Arabidopsis thaliana ATR2 polypeptide, an Oryzya sativa EUGT 11 polypeptide, a SrKAHe1 polypeptide, a Stevia rebaudiana CPRS polypeptide, an Stevia rebaudiana UGT85C2 polypeptide, an Stevia rebaudiana UGT74G1 polypeptide, a Stevia rebaudiana UGT76G1 polypeptide, a Stevia rebaudiana UGT91D2 variant or functional homolog, and a UGT91D2e-b polypeptide.

Steviol glycoside-producing *S. cerevisiae* strains were constructed using methods as described in WO 2011/153378, WO 2013/022989, WO 2014/122227, and WO 2014/122328, each of which is incorporated by reference in their entirety. The following sequences were used for construction of a parent strain (Strain A): a recombinant gene encoding a *Synechococcus* sp GGPPS polypeptide (SEQ ID NO:6), a recombinant gene encoding a truncated *Zea mays* CDPS polypeptide (SEQ ID NO:7), a recombinant gene encoding an *Arabidopsis thaliana* KS polypeptide (SEQ ID NO:8), a recombinant gene encoding a recombinant *Stevia rebaudiana* KO polypeptide (SEQ ID NO:9, SEQ ID NO:10), a recombinant gene encoding an *Arabidopsis thaliana* ATR2 polypeptide (SEQ ID NO:11, SEQ ID NO:12), a recombinant gene encoding an *Oryza saliva* EUGT 11 polypeptide (SEQ ID NO:13), a recombinant gene encoding an SrKAHe1 polypeptide (SEQ ID NO:14, SEQ ID NO:15), a recombinant gene encoding an *Stevia rebaudiana* CPR8 polypeptide (SEQ ID NO:16, SEQ ID NO:17), a recombinant gene encoding an *Stevia rebaudiana* UGT85C2 polypeptide (SEQ ID NO:2), a recombinant gene encoding an *Stevia rebaudiana* UGT74G1 polypeptide (SEQ ID NO:1), a recombinant gene encoding an *Stevia rebaudiana* UGT76G1 polypeptide (SEQ ID NO:3), and a recombinant gene encoding an *Stevia rebaudiana* UGT91D2 variant (or functional homolog), UGT91D2e-b, (SEQ ID NO:4) polypeptide produced steviol glycosides.

The UGT91D2e-b variant of UGT91D2 (SEQ ID NO:5 from PCT/US2012/050021) includes a substitution of a methionine for leucine at position 211 and a substitution of an alanine for valine at position 286. (Additional variants, except T144S, M152L, L213F, S364P, and G384C variants, described in Table 12 and Example 11 of PCT/US2012/050021, which is hereby incorporated by reference in its entirety, could be used.) GeneArt codon-optimized sequence encoding a *Stevia rebaudiana* UGT91D2e-b with the amino acid modifications L211M and V286A (SEQ ID NO:4 for amino acid sequence; codon optimized nucleotide sequence is set forth in SEQ ID NO:5).

Strain B is derived from the parent strain described above and additionally includes a codon-optimized CPR1 from *Stevia rebaudiana* (SEQ ID NO:18 corresponding to amino acid SEQ ID NO:19).

In one embodiment, the engineered yeast expresses one or more exogenous nucleic acid(s) encoding one or more of the following proteins heterologous to the yeast: GGPPS polypeptide, an ent-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91D2 polypeptide, and a EUGT11 polypeptide.

In another embodiment, the engineered yeast expresses one or more exogenous nucleic acid(s) encoding one or more of the following proteins heterologous to the yeast: a GGPPS polypeptide, a truncated *Zea mays* CDPS polypeptide, an *A. thaliana* KS polypeptide a *S. rebaudiana* KO polypeptide, an *A. thaliana* ATR2 polypeptide, an *O. sativa* EUGT 11 polypeptide, a SrKAHe1 polypeptide, a *S. rebaudiana* CPR8 polypeptide, an *S. rebaudiana* UGT85C2 polypeptide, an *S. rebaudiana* UGT74G1 polypeptide, a *S. rebaudiana* UGT76G1 polypeptide, a *S. rebaudiana* UGT91D2 variant or functional homolog, and a UGT91D2e-b polypeptide The engineered host cells (e.g., yeast cells) can be used to produce the desired steviol glycosides such as rebaudioside M, rebaudioside D, and rebaudioside A by fermentation.

"Fermentation" as used here refers to the assimilation of the medium such as the carbohydrates to produce the desired steviol glycosides through aerobic fermentation. The term "medium" or grammatical equivalents such as "media" refers to a liquid composition in which the engineered yeast or fungus can be maintained, grown, or fermented, or combinations thereof. A "medium" may also be referred to as a "broth" or "cell culture," and terms such as "fermentation" that qualifies the term "medium" and its equivalents may be used to more specifically define the type of cellular activity that is occurring in the medium.

A medium can be defined with regards to the components present in the medium, and amounts thereof, including, but not limited to: (a) carbon sources, including carbohydrates such as glucose and starch products such as maltodextrin; (b) nitrogen sources, such as yeast nitrogen base, ammonium hydroxide, urea, ammonium sulfate, yeast extract or any combination thereof; (c) salts, such as potassium phosphate (monobasic, dibasic), magnesium sulfate, sodium chloride, and calcium chloride; (d) vitamins, such as biotin, calcium pantothenate, folic acid, (myo)-inositol, nicotinic acid, p-aminobenzoic acid, pyridoxine HCl, riboflavin, thiamine HCL, and citric acid; and/or (e) trace metals such as boric acid, copper sulfate, cobalt chloride, calcium chloride, potassium iodide, ferric chloride, magnesium sulfate, manganese chloride, sodium molybdate, and zinc sulfate. The medium can also be defined with regards to its pH, and biocompatible acids, bases, and buffers that are used to control the pH in the medium.

Fermentation of the engineered yeast can be performed using starch and/or sugar containing plant material derivable from any plant and plant part, such as tubers, roots, stems, leaves and seeds. Starch and/or sugar comprising plant material can be obtained from cereal, such as barley, wheat, maize, rye, sorghum, millet, barley, potatoes, cassava, or rice, and any combination thereof. The starch- and/or sugar comprising plant material can be processed, such as by methods such as milling, malting, or partially malting. In some embodiments, the fermentation media includes a treated starch. For example, the fermentation media can include a partially hydrolyzed starch. The partially hydrolyzed starch can include high molecular weight dextrins and high molecular weight maltodextrins. A partially hydrolyzed starch product can be used that have amounts of starch and starch degradation products within desired ranges.

Fermentation can be carried out under conditions and in medium suitable for production of the desired steviol glycosides such as rebaudioside M, rebaudioside D, and rebaudioside A. The fermentation conditions generally use oxygen (aerobic conditions), a carbon source, and a nutrient (nitrogen) base. Fermentation can be carried out using a fed batch or continuous process. The fermentation minimal medium includes glucose (5 g/L), ammonium sulfate (5 g/L), potassium dihydrogenphosphate (3 g/L), magnesium sulphate (0.5 g/L), trace elements, and vitamins (e.g., see, Verduyn, C. et al. (1992) Yeast 8, 501-517). The pH of the fermentation media can be at about pH 4 to pH 5 and the fermentation can be carried out at a temperature at about 30° C. In some embodiments, fermentation can be carried out using a first growth phase in base medium, followed by a longer feeding phase using a glucose-containing defined feed medium (with trace metals, vitamins, and salts).

In other embodiments, fermentation may be carried out using a pH greater than 5.0. In some embodiments, the pH may range from about 5.5 to 8 or 5.8 to 7.5. In some embodiments, the engineered yeast may be grown initially at a lower pH such as less than 6.0 and fermentation carried out at a higher pH such as greater than 5.0. Other methods of fermentation for producing the desired steviol glycosides are described in the application titled "Fermentation Methods for Producing Steviol Glycosides Using High pH and Compositions Obtained Therefrom," U.S. Pat. App. No. 62/168, 345, and in International PCT application titled "Fermentation Methods for Producing Steviol Glycosides," and filed concurrently with the present application, which are each hereby incorporated by reference in their entirety.

Optionally, fermentation can be carried out in media containing other intermediates such as steviol, rebudioside A, stevioside, rubusoside, steviol monoside, steviolbioside, dulcoside A, rebaudioside C, rebaudioside E, and the like.

The fermentation step can also be referred to as a "steviol glycoside producing step." In some embodiments, the fermentation medium is maintained at a temperature less than 40° C. during the fermentation step. In some embodiments, the fermentation medium is maintained at a temperature in the range of about 25 to 35° C. during the fermentation step.

After fermentation, but before any treatment (e.g., heat treatment) to release or enrich for the desired steviol glycosides, the fermentation broth may contain only a fraction of the desired glycosides, with the majority of the desired glycosides within the engineered host cell. Disclosed are methods of releasing or enriching for the desired glycoside from the host cell by using heat.

The heat treatment may be carried out on the whole cell fermentation broth, which contains the engineered yeast capable of producing the desired steviol glycosides and the desired steviol glycoside products. In other embodiments, the engineered yeast after fermentation but before any treatment (e.g. heat treatment) may be separated from the fermentation broth and transferred into any suitable composition such as a liquid media.

The fermentation broth or composition containing the transferred yeast cells may be heated at temperatures ranging from 50° C. to 95° C. In other embodiments, the heating is carried out at temperatures from 70° C. to 95° C. Heating is carried out for 5 minutes to 48 hours. In some embodiments, heating is at 70° C. to 95° C. for 5 minutes to 2 hours, 95° C. for 5 minutes to 1 hour, 75° C. for 5 minutes to 2 hours, or 50° C. for 24 hours. In some embodiments, the heating is at 70° C. to 95° C. for 5 minutes or from 70° C. to 95° C. for 2 hours.

In some embodiments, the heat treatment releases the steviol glycosides into the medium or enriches the steviol glycoside content of the medium such that the extracellular glycoside content is greater than 90% of the total (i.e., both intracellular and extracellular) glycoside content in the fermentation broth or composition. In some embodiments, the heat treatment step releases steviol glycosides into the fermentation medium such that the extracellular steviol glycoside content is greater than 80%, 85%, 91%, 92%, 93%, 94%, 95%, 96%, 97%, 98%, or 99%, of the total (i.e., both intracellular and extracellular) steviol glycoside content in the fermentation broth or composition. In some embodiments, the heat treatment step releases steviol glycosides into the fermentation medium such that the extracellular steviol glycoside content is in the range of about 80 to 100%, 85 to 100%, 90 to 100%, 90 to 99%, 92 to 98%, or 90 to 95% of the total (i.e., both intracellular and extracellular) steviol glycoside content in the fermentation broth or composition.

In some embodiments, the heat treatment of the fermentation broth or composition releases Reb A, Reb 13, Reb M, Reb D or combinations thereof. In some embodiments, the heat treatment enriches for Reb A such that the extracellular Reb A is greater than 50% of the total (i.e., both intracellular and extracellular) Reb A present in the fermentation broth or composition. In some embodiments, the extracellular Reb A is greater than 40%, 45%, 48%, 52%, 55%, 57%, 60%, 62%, 65%, 67%, 70%, 75%, 80%, 85%, 90%, 95%, or 99% of the total (i.e., both intracellular and extracellular) Reb A present in the fermentation broth or composition. In some embodiments, the Reb A amount, can be released extracellularly in the range of about 30% to about 100%, about 50% to about 100%, about 80% to about 90% of the total amount of Reb A produced during the fermentation.

In some embodiments, the heat treatment enriches for Reb D and/or Reb M such that the Reb D and/or Reb M released extracellularly is greater than 33% of the total (i.e. both intracellular and extracellular) Reb D and/or Reb M present in the fermentation broth or composition. In some embodiments, the extracellular Reb D, Reb M, and/or the total of Reb D and Reb M is greater than 40%, 45%, 48%, 52%, 55%, 57%, 60%, 62%, 65%, 67%, 70%, 75%, 80%, 85%, 90%, 95%, or 99% of the total (i.e., both intracellular and extracellular) Reb D, Reb M, and/or the total of Reb D and Reb M present in the fermentation broth or composition. In some embodiments, the combined amount of Reb D and Reb M, released extracellularly can be present in the range of about 30% to about 100%, about 50% to about 100%, about 80% to about 90% of the total amount of Reb D and/or Reb M present in the fermentation broth or composition.

In other embodiments, the Reb D released, can be present extracellularly in the range of about 30% to about 100%, about 50% to about 100%, about 80% to about 90% of the total amount of Reb D present in the fermentation broth or composition.

In other embodiments, the Reb M released, can be present extracellularly in the range of about 30% to about 100%, about 50% to about 100%, about 80% to about 90% of the total amount of Reb M present in the fermentation broth or composition.

In some embodiments, the Reb B released, can be present extracellularly in the range of about 25% to about 100%, about 30% to about 95%, about 40% to about 80% of the total amount of Reb B present in the fermentation broth or composition. In some embodiments, the extracellular Reb B is greater than 30%. 33%. 35%, 40%, 45%, 48%, 52%, 55%, 57%, 60%, 62%, 65%, 67%, 70%, 75%, 80%, 85%, 90%, 95%, or 99% of the total (i.e., both intracellular and extracellular) Reb B present in the fermentation broth or composition. In some embodiments, the disclosed heat treatment does not result in significant degradation from Reb DM and/or Reb A to Reb B.

In some embodiments, the disclosed heat treatment results in the release of the desired glycosides yet does not result in extensive lysis of the cell. Cell lysis may be determined, for example, by the amount of nitrogen or phosphorus or both released into the fermentation broth (e.g., cell free) or composition after the fermentation and heat treatment. In some embodiments, the heating of the fermentation broth or composition does not increase nitrogen and/or phosphorus content in the cell free fermentation broth or composition. In some embodiments, the extracellular nitrogen content in the cell free fermentation broth or composition after the heat treatment is not increased by more than 45% of the total (i.e. extracellular and intracellular) nitrogen present in the whole cell fermentation broth or composition. In some embodiments, the extracellular phosphorous content in the fermentation broth or composition after the heat treatment is not increased by more than 70% of the total (i.e. extracellular and intracellular) phosphorous present in the cell-containing fermentation broth or composition.

In still other embodiments, the extracellular nitrogen content is not increased by more than 45% of the total nitrogen present in the cell-containing fermentation broth or composition and/or the extracellular phosphorous content in the fermentation broth or composition after the heat treatment is not increased by more than 70% of the total phosphorous present in the cell-containing fermentation broth or composition when heated at 70° C. to 95° C. for 5 minutes to 2 hours.

In some embodiments, when the fermentation medium or composition is heated at 50 to 95° C. for 5 minutes to 48 hours, the extracellular nitrogen content is not increased by more than 30%, 33%, 35%, 37%, 40%, 42%, 47%, or 50% of the total nitrogen present in the cell-containing fermentation broth or composition. In some embodiments, when the fermentation medium or composition is heated at 50 to 95° C. for 5 minutes to 48 hours, the extracellular phosphorus content is not increased by more than 50%, 55%, 60%, 63%, 65%, 67%, 73%, 75%, 77%, or 80% of the total phosphorus present in the cell-containing fermentation broth or composition.

The intracellular and/or extracellular content of various components of the fermentation broth or composition (e.g., steviol glycosides, nitrogen, or phosphorus) can be determined as described in Example 1.

The heat treatment of the fermentation broth or composition may also be evaluated based on the cell viability. While the desired glycosides may be released from the yeast cell into the fermentation broth or composition, the yeast viability is decreased while limiting cell lysis. Cell lysis may be determined, for example, by plating the whole cell broth on Potato Dextrose Antibiotic Agar or by cell viability counter (e.g., Cellometer™).

Heating may be carried out by using a heat exchanger in which heat is transferred to hot water or steam. In some embodiments, heating may be carried out using a heat exchanger with a holding loop, direct steam injection, or bulk heating of the material utilizing steam applied to a jacketed vessel. In some embodiments, the yeast may be concentrated for example, by centrifugation or filtration, before a heat treatment. In other embodiments, the centrifuged or filtered yeast may be transferred into other suitable media or composition and then used for heating.

Following the release of the desired recombinant product (e.g. steviol glycosides) from the host cell into the medium, thereby enriching for the desired product, various procedures can be used for further isolation and purification of the desired recombinant product. Such procedures include centrifugation, ultrafiltration, precipitation and chromatographic procedures.

After the steviol glycosides are released or enriched, the steviol glycosides may be further purified by preparative HPLC as described, for example in International Patent Application Publication No. WO 2009/140394, which is incorporated by reference in its entirety.

The fermentation broth or composition after the heat treatment can then be centrifuged or filtered to remove the engineered cells. The fermentation broth can optionally be treated to remove low molecular weight components (glucose, basic nutrients, and salts), such as by membrane dialysis.

If it is desired to provide a composition with steviol glycosides including Reb A, Reb B, Reb M, Reb D, and combinations thereof in enriched or purified form, or where Reb A, Reb B, Reb M, Reb D, and combinations thereof are separated from other steviol glycosides, or separated from one another, further purification can be carried out. Such enrichment or purification of steviol glycoside components can be carried out on liquid fermentation media, or the fermentation media can then be dried down prior to purification. For example, fermentation media can be dried down using lyophilization to form a dry composition (e.g., powder or flakes) including steviol glycosides with Reb A, Reb B, Reb M, Reb D, and combinations thereof that can be subsequently processed.

In some embodiments, dried fermentation broth or composition enriched for steviol glyosides including Reb A, Reb B, Reb M, and/or Reb D, may be used as the starting material for purification. For example, a solvent or solvent combination can be added to the dried fermentation broth to dissolve or suspend materials that include the steviol glycosides. An exemplary combination for dissolving the steviol glycosides is a mixture of water and an alcohol (e.g., 50:50 ethanol:water). To facilitate dissolving or resuspending, the dried broth materials can be heated at a temperature above room temperature, such as in the range of 40° C.-60° C. Mechanical disruption of the dried fermentation broth materials can also be performed, such as by sonication. The dissolved or resuspended fermentation broth materials can be filtered using a micron or sub-micron filtration system prior to further purification, such as by preparative chromatography.

Dried fermentation broth or composition enriched for steviol glycoside compounds can be subjected to other purification processes, such as reverse phase liquid chromatography. A suitable resin can be used to retain steviol glycoside compounds in the column, with removal of hydrophilic compounds which get washed through the column with a liquid such as water. Elution of steviol glycosides including Reb A, Reb B, Reb M, Reb D, and combinations thereof from the column can be accomplished using a suitable solvent or solvent combination such as acetonitrile or methanol.

In some embodiments, the steviol glycosides such as Reb A, Reb B, Reb M, Reb D, and combinations thereof can be purified using preparative liquid chromatography, such as high pressure liquid chromatography (HPLC) or ultra high pressure liquid chromatography (UHPLC). A steviol glycoside composition with Reb A, Reb B, Reb M, Reb D, and combinations thereof can be dissolved in a mobile phase, such as a mixture of water and an solvent (e.g., methanol, ethanol, acetonitrile) at a desired ratio (e.g., 60% water, 40% methanol, v/v). The composition can also be heated to enhance dissolution of the steviol glycoside material, such as heating at about 50° C. The solution can also be filtered prior to injection into the column, such as using a 0.2 µm filter. Phenomenex Kinetex XB-C18 5 µm, core-shell silica solid support, and stationary phase of C18 with iso-butyl side chains and TMS endcapping. The flow rate through the column can be based on column properties (such as about 20 mL/min), with a maximum pressure of 400 bar. Reb A, Reb B, Reb M, Reb D, and combinations thereof can be identified by their elution times from the column. In exemplary flow conditions Reb A, Reb B, Reb M, Reb D, and combinations thereof can elute from the column within 60 minutes. One of skill in the art will appreciate that the elution times for the Reb A, Reb B, Reb M, Reb D, and combinations thereof can vary with changes in solvent and/or equipment. One of skill in the art will also understand that although the process described below assumes certain order of the described steps, this order can be altered in some cases.

In some embodiments, the fermentation broth or composition enriched for steviol glyosides including Reb A, Reb M, and/or Reb D, may be dried and used as the starting material for further purification. A steviol glycoside composition with Reb A, Reb M, Reb D, and combinations thereof can be dissolved in water and passed through adsorption chromatographic column to remove hydrophilic impurities in the composition. Adsorbed steviol glycosides can be desorbed from the column with ethanol/water mixture. Upon removal of the ethanol, the steviol glycoside liquid stream can be further purified with ion exchange chromatography to remove ions and color bodies. Additional treatment with activated carbon could be performed. To further separate specific steviol glycosides from others, a crystallization step could be used. The crystals may be enriched with Reb M, Reb D, Reb A, or other steviol glycosides. The crystals can be dried under heat and vacuum or can be re-slurried with water and spray dried.

Example 1

Production of Reb D, Reb M and Reb A in Fed Batch Fermentation with Ammonium Hydroxide as the Primary Nitrogen Source For inoculum preparation, a yeast strain designated strain B was cultured in 150 mLs of seed flask medium in 1 liter shake flasks at 250 rpm and 30° C. for 20-24 hours.

TABLE 1

| Seed Flask Medium | | | |
|---|---|---|---|
| Component | Formula | Concentration | Units |
| Biospringer 0251 yeast extract | | 7.5 | g/L |
| Glucose monohydrate | $C_6H_{12}O_6*H_2O$ | 22.0 | g/L |

For the fermentation, 75 mL of seed culture was transferred into initial fermentation medium (Tables 2, 3 and 4) with a starting volume of 0.75 liters. Temperature was maintained at 30° C. throughout. The air flow rate was 1.75 SLPM and the agitation rate was automatically controlled to increase in a stepwise manner from 400 to 900 rpm during the fermentation. Glucose concentration was kept limiting by controlling flow rates of feed medium (Table 5). A 2-phase feeding strategy involved an initial exponential phase beginning at 10 hours with a growth rate of u=0.12 l/h while the second phase of feeding (or feed phase II) started at 33 hours with a constant flow rate of 0.180 mls/minute. Feeding was continued until a final volume of 1.95 liters was obtained by 120 hours.

pH was maintained at pH 5 with 12% NH$_4$OH throughout fermentation. Antifoam addition was controlled by utilization of foam control probes with 10 wt % antifoam solution (Ivanhoe 1163B). The medium was based on Verduyn et al (Verduyn C, Postma E, Scheffers W A, Van Dijken J P. Yeast. 1992 July; 8(7):501-17) with modifications as described in Tables 2 through 5.

TABLE 2

| Initial Fermentation Medium | | | |
|---|---|---|---|
| Component | Formula | Concentration | Units |
| Glucose monohydrate | $C_6H_{12}O_6* H_2O$ | 22.0 | g/L |
| Ammonium sulfate | $(NH_4)_2SO_4$ | 5.0 | g/L |

TABLE 2-continued

Initial Fermentation Medium

| Component | Formula | Concentration | Units |
|---|---|---|---|
| Monobasic potassium phosphate | $KH_2PO_4$ | 3.0 | g/L |
| Magnesium sulfate heptahydrate | $MgSO_4 * 7 H_2O$ | 0.5 | g/L |
| Trace metals stock | | 10.0 | ml/L |
| Vitamin stock | | 12.0 | ml/L |

TABLE 3

Trace Metals Stock Solution

| Component | Formula | Concentration | Units |
|---|---|---|---|
| Disodium edetate | $C_{10}H_{14}N_2Na_2O_8 * 2H_2O$ | 15 | g/L |
| Zinc sulfate heptahydrate | $ZnSO_4 * 7H_2O$ | 4.5 | g/L |
| Manganese (II) chloride tetrahydrate | $MnCl_2 * 4H_2O$ | 1.026 | g/L |
| Cobalt (II) chloride hexahydrate | $CoCl_2 * 6H_2O$ | 0.32 | g/L |
| Copper (II) sulfate heptahydrate | $CuSO_4 * 5H_2O$ | 0.3 | g/L |
| Sodium molybdate dihydrate | $Na_2MoO_4 * 2H_2O$ | 0.4 | g/L |
| Calcium chloride dihydrate | $CaCl_2 * 2H_2O$ | 3 | g/L |
| Iron (II) sulfate heptahydrate | $FeSO_4 * 7H_2O$ | 3 | g/L |
| Boric acid | $H_3BO_3$ | 1 | g/L |
| Potassium iodide | KI | 0.1 | g/L |

TABLE 4

Vitamin Stock Solution

| Component | Formula | Concentration | Units |
|---|---|---|---|
| d-Biotin | $C_{10}H_{16}N_2O_3S$ | 50 | mg/L |
| Calcium pantothenate | $C_{18}H_{32}CaN_2O_{10}$ | 1000 | mg/L |
| Nicotinic acid | $C_6H_5NO_2$ | 1000 | mg/L |
| Thiamine hydrochloride | $C_{12}H_{17}ClN_4OS \cdot HCl$ | 1000 | mg/L |
| Pyridoxine hydrochloride | $C_8H_{11}NO_3 \cdot HCl$ | 1000 | mg/L |
| p-aminobenzoic acid | $C_7H_7NO_2$ | 200 | mg/L |
| myo-inositol | $C_6H_{12}O_6$ | 25000 | mg/L |

TABLE 5

Fermentation Feed Medium

| Component | Formula | Concentration | Units |
|---|---|---|---|
| Glucose monohydrate | $C_6H_{12}O_6 * H_2O$ | 660 | g/L |
| Urea (in urea treatments only) | $NH_2CONH_2$ | 33 | g/L |
| Antifoam | | 1.3 | g/L |
| Potassium sulfate | $K_2SO_4$ | 4.2 | g/L |
| Sodium sulfate | $Na_2SO_4$ | 0.336 | g/L |
| Magnesium sulfate heptahydrate | $MgSO_4 * 7H_2O$ | 6.12 | g/L |
| Monobasic potassium phosphate | $KH_2PO_4$ | 10.8 | g/L |
| Trace metal stock | | 14.4 | mL/L |
| Vitamin stock | | 14.4 | mL/L |

Example 2

Enrichment or Release and Analysis of Steviol Glycosides

The fermentation broth generated from a recombinant yeast fermentation as described in Example 1 was used. The measurement of total steviol glycosides including intracellular and extracellular concentrations as well as the total nitrogen content (intracellular and extracellular) and total phosphorous content (intracellular and extracellular) was carried out by agitating the fermentation samples including the yeast cells to ensure that yeast cells were mixed and did not settle to the bottom of the vial. 100 μL of the mixed fermentation broth were pipetted into a 2 mL microcentrifuge tube. 900 μL of 61% methanol (extraction solvent) was added into the 2 ml microcentrifuge tube and agitated by placing on a sample rotator for 10 min to extract the steviol glycosides. The samples were then centrifuged at 10K rpm in a microcentrifuge for 3 min and the clarified supernatant was pipetted into an autosampler vial for analysis.

The fermentation broth (including cells) was heated at various temperatures and for various times. Heating was accomplished using a hot water bath and the sample was prepared as follows: 1 ml of the fermentation broth (including cells) was placed into a headspace vial for each temperature and time point studied. The vials were sealed and placed into the water bath and allowed to equilibrate for 5 minutes at each temperature studied prior to maintaining the samples at the desired temperature for the desired amount of time. At the end of the designated time, the samples were removed from the water bath and were cooled at 4° C. 4 ml of sterile water was added to each vial after which the sample was transferred to a 14 ml sterile tube. Samples were vortexed and 1 ml was removed for determining cell viability by the plating method. The remainder of the sample was centrifuged at 4700 rpm for 30 minutes at room temperature to obtain clear, cell-free supernatant. The cell-free supernatant was removed for further analysis, for example the extracellular content of steviol glycosides, nitrogen, and phosphorus in the fermentation medium (Phosphorous via ICP, Nitrogen via Antek and glycoside via UHPLC).

The amount of glycosides released into the fermentation broth after the heat treatment was determined. Reb A, Reb D and Reb M were measured by ultra-performance liquid chromatography (UPLC). The cell free supernatant was also used to evaluate nitrogen and phosphorous release into the fermentation broth. Nitrogen levels were analyzed using the combustion method and an ANTEK™ nitrogen analyzer (Antek 9000 nitrogen detector utilizing nitrogen combustion and reaction with ozone to produce metastable nitrogen dioxide, which is detected via chemiluminescence and phosphorous levels were analyzed using inductively coupled plasma spectrometry ICP, Perkin Elmer Optima 3200DV, UV detection at 213.617 nm, samples dissolved in 0.5% $HNO_3$). Yeast viability was determined using the Potato Dextrose Antibiotic Easy gel plates (Microbiology Labs test kits), incubated at room temperature for 5 days.

UPLC Method for Glycoside Separation

The steviol glycosides were separated using an Eclipse C18 Plus RRHD column (3 mm×150 mm×1.8 um) with Eclipse Plus C18 guard (column 3 mm×5 mm×1.8 um). The mobile phase used was channel A: 10 mM phosphate buffer, pH 2.6 and channel B acetonitrile. The flow rate was 0.6 ml/min, the column temperature was 40° C. and the detection was performed at ultraviolet absorption of 210 nm. The gradient elution profile in which the ratio of phosphate buffer to acetonitrile changed is shown below:
i. Initial: 80% A/20% B
ii. 7 minutes: 70% A/30% B
iii. 12 minutes: 70% A/30% B
iv. 15 minutes: 45% A/55% B
v. 18 minutes: 45% A/55% B
vi. 20 minutes: 20% A/80% B
vii. 25 minutes: 20% A/80% B
viii. 27 minutes: 15% A/85% B
ix. 30 minutes: 15% A/85% B
x. 30.5 minutes: 80% A/20% B
xi. 35 minutes: 80% A/20% B The UPLC results, shown as the % of extracellular Reb A, Reb D & M released from the yeast cell after the heat treatment is shown in Table 6. The % of the extracellular nitrogen and phosphorus are also shown.

Total nitrogen in the fermentation broth including cells was determined using a Leco Nitrogen Analyzer (Leco TruMac N, St. Joseph, Mich.). 1 ml of homogeneously mixed fermentation broth including cells were applied to a nickel lined ceramic combustion container for nitrogen combustion analysis.

Total phosphorus in the fermentation broth including cells was determined by ashing 5 mL of homogenously mixed fermentation broth with a propane torch in a ceramic crucible. The resultant ash was held at 525° C. overnight prior to dissolving the ash with 10 mls of 0.5% $HNO_3$. Phosphorus content in the nitric acid solution was determined using ICP.

TABLE 6

| Heat treatment condition Temperature, ° C. | Time hr | % extracellular Reb D&M | % extracellular Reb A | % extracellular Reb B | Reb B (% extracellular) | % extracellular N | % extracellular P |
|---|---|---|---|---|---|---|---|
| 24 | 1 | 34% | 48% | 20% | 28% | 20% | 45% |
|  | 2 | 34% | 48% | 21% | 28% | 21% | 45% |
|  | 24 | 43% | 52% | 25% | 30% | 25% | 51% |
|  | 48 | 47% | 58% | 30% | 34% | 30% | 56% |
|  | 70 | 48% | 59% | 31% | 34% | 31% | 55% |

| Temperature, ° C. | Time, hr | % extracellular D&M | % extracellular A | % extracellular) B | % extracellular N | % extracellular P |
|---|---|---|---|---|---|---|
| 50 | 0.08 | 44% | 54% | 30% | 23% | 46% |
|  | 0.5 | 56% | 67% | 36% | 28% | 55% |
|  | 1 | 72% | 88% | 41% | 37% | 65% |
|  | 1.5 | 76% | 85% | 44% | 40% | 67% |
|  | 2 | 88% | 91% | 46% | 50% | 76% |
|  | 24 | 98% | 99% | 58% | 88% | 93% |
|  | 48 | 95% | 97% | 60% | 91% | 92% |
|  | 70 | 93% | 96% | 61% | 91% | 97% |
|  | 72 | 92% | 96% | 60% | 93% | 95% |
|  | 96 | 91% | 96% |  | 91% | 95% |
|  | 120 | 87% | 92% |  | 92% | 95% |

| Temperature, ° C. | Time, hr | % extracellular D&M | Reb B (% extracellular) | % extracellular N | % extracellular P |
|---|---|---|---|---|---|
| 70 | 0.08 | 101% |  | 36% | 64% |
|  | 0.25 | 101% | 45% | 35% | 62% |
|  | 0.5 | 101% |  | 36% | 64% |
|  | 0.75 | 99% | 45% | 35% | 66% |
|  | 1 | 101% |  | 36% | 66% |
|  | 1.5 | 101% | 46% | 37% | 65% |
|  | 2 | 99% |  | 37% | 64% |

| Temperature, ° C. | Time, hr | % extracellular D&M | % extracellular A | Reb B (% extracellular) | % extracellular N | % extracellular P |
|---|---|---|---|---|---|---|
| 75 | 0.08 | 96% | 92% | 44% | 35% | 65% |
|  | 0.5 | 98% | 94% | 45% | 36% | 68% |
|  | 1 | 96% | 94% | 46% | 35% | 69% |
|  | 2 | 95% | 93% | 47% | 36% | 67% |
|  | 24 | 80% | 82% | 69% | 38% | 74% |
|  | 48 | 74% | 78% | 86% | 40% | 82% |
|  | 70 | 68% | 72% | 98% | 44% | 88% |

TABLE 6-continued

| Temperature, °C. | Time, hr | % extracellular D&M | % extracellular A | Reb B (% extracellular) | % extracellular N | % extracellular P |
|---|---|---|---|---|---|---|
| 95 | 0.08 | 98% | 93% | 47% | 32% | 65% |
|  | 0.25 | 100% | 99% | 49% | 33% | 65% |
|  | 0.5 | 101% | 99% | 53% | 36% | 66% |
|  | 1 | 96% | 91% | 55% | 35% | 67% |

As can be seen from Table 6, a heat treatment at a higher temperature and for a shorter time results in an increase in the release of the Reb A, Reb D and Reb M from within the yeast cell while affecting a heat kill but with minimal cell lysis as evaluated by the amount of nitrogen and phosphorus in the medium after the heat treatment. The table also shows that at higher temperatures (50° C., 75° C. and 95° C. and longer times), Reb DM and RebA can degrade to Reb B resulting in a lower Reb DM content in the broth and an increase in Reb B content.

Viable yeast counts after heat treatment are shown in Table 7. It takes between 2 and 24 hours at 50° C. to kill the yeast while no more than 5 minutes at 75° C. or 95° C. to kill the yeast.

TABLE 7

| Temperature | Time | YM (CFU/ml) |
|---|---|---|
| 24 C. | 24 h | 1.02E+09 |
| 50 C. | 1 h | 2.03E+04 |
|  | 2 h | 600 |
|  | 24 h | <10 |
|  | 48 h | <10 |
|  | 72 h | <10 |
| 75 C. | 0.08 h | <10 |
|  | 0.5 h | <10 |
|  | 1 h | <10 |
|  | 2 h | <10 |
|  | 24 h | <10 |
|  | 48 h | <10 |
|  | 70 h | <10 |
| 95 C. | 0.08 h | <10 |
|  | 1 h | <10 |

Example 3

Fermentation broth from a strain designated A in a two-phase process was heat treated at 75° C. for one hour. The two phase rates of feeding are shown below:

| Strain | pH control | Phase I | Phase II |
|---|---|---|---|
| B | 5.0 | 0.12 u | 0.166 mL/min |

Figure 5:
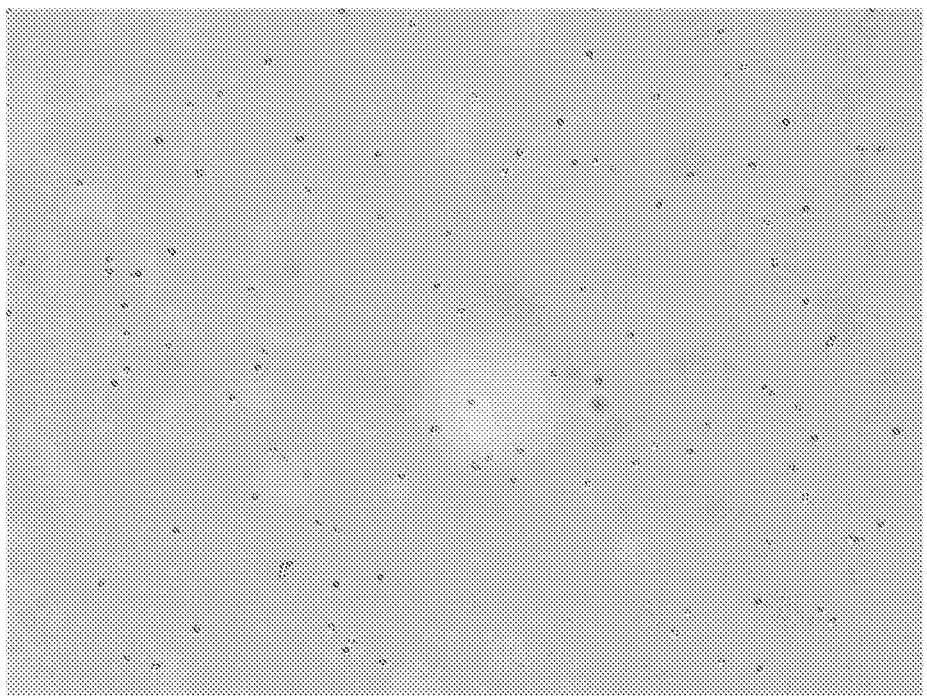
FIG. 5A is a digital image of a bright field microscopy image before heat treatment.
FIG. 5B is a digital image of a bright field microscopy image after heat treatment.
Figure 5:
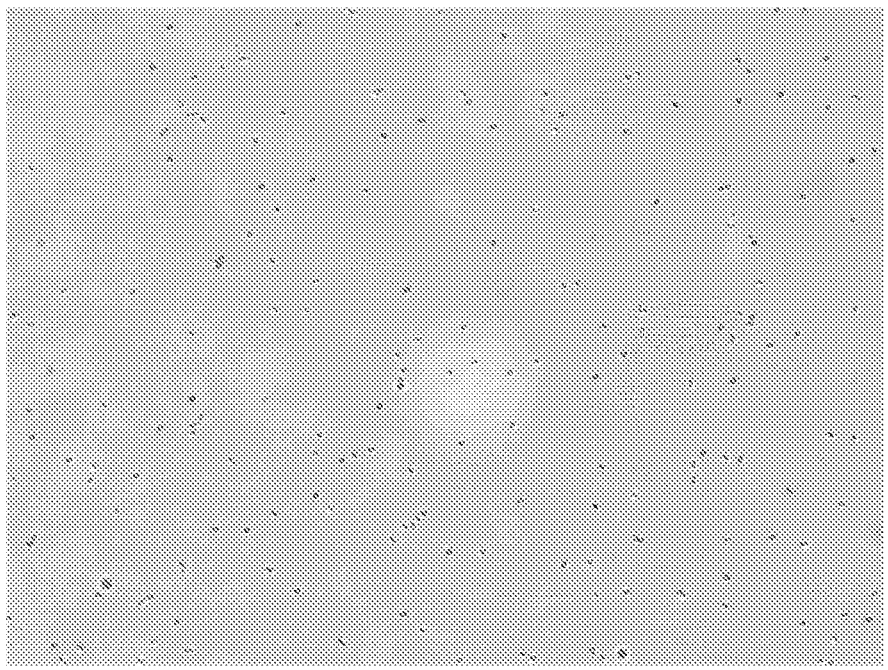

Yeast cells were stained by the fluorescent dyes based on the Nexcelom Cellometer method. Live cells before heat treatment appeared green under microscope and dead cells after heat treatment appeared red. Bright field microscopy images showed a lack of debris after heat treatment (compare FIG. 5A with FIG. 5B) indicating that the yeast cells were intact even after heat treatment.

What is claimed is:

1. A method of releasing steviol glycosides from a yeast host cell, comprising the steps of:
   (a) providing a fermentation medium, comprising the host cell producing one or more steviol glycosides; and
   (b) releasing the one or more steviol glycosides from the host cell by heating the fermentation medium to a temperature in a range from 50° C. to 95° C. for 5 minutes to 48 hours, wherein the one or more steviol glycosides are released from an intracellular portion of the host cell into an extracellular portion of the fermentation medium;
   wherein the extracellular nitrogen content in the fermentation medium after the heat treatment is not increased by more than 45% of the total extracellular and intracellular nitrogen content in the fermentation medium;
   wherein the extracellular phosphorous content in the fermentation medium after the heat treatment is not increased by more than 70% of the total extracellular and intracellular phosphorous content in the fermentation medium; and
   wherein the one or more steviol glycosides is rebaudioside M (Reb M), rebaudioside D (Reb D), rebaudioside A (Reb A), rebaudioside B (Reb B), or combinations thereof.

2. The method of claim 1, wherein the fermentation medium is heated to the temperature in the range from 70° C. to 95° C. for 5 minutes to 2 hours.

3. The method of claim 1, wherein the fermentation medium is heated to about 50° C. for 24 hours.

4. The method of claim 1, wherein the fermentation medium is heated to about 75° C. for 5 minutes to 2 hours.

5. The method of claim 1, wherein the fermentation medium is heated to about 95° C. for 5 minutes to 1 hour.

6. The method of claim 1, wherein the released steviol glycosides can be further separated or purified from the host cells.

7. The method of claim 1, wherein the yeast is selected from the group consisting of genus, Candida, Pichia (Hansenula), Kloeckera (Hanseniaspora), Kluyveromyces, Rhodotorula, Torulopsis, Zygosaccharomyces, Saccharomycete, Yarrowia, and Saccharomyces.

8. The method of claim 1, wherein the host cell is Saccharomyces cerevisiae.

9. The method of claim 1, wherein the Reb M, Reb D, Reb A, Reb B, or combinations thereof released are greater than 90% of the Reb M, Reb D, Reb A, Reb B, or combinations produced by the host cell.

10. The method of claim 1, wherein an amount of Reb D and/or an amount of Reb M released extracellularly is greater than 33% of a total intracellular and an extracellular amount of Reb D and/or Reb M produced.

11. The method of claim 1, wherein the amount of Reb D released is greater than 30% of the total intracellular and extracellular amount of Reb D produced during fermentation.

12. The method of claim 1, wherein the amount of Reb M released is greater than 30% of the total intracellular and extracellular amount of Reb M produced during fermentation.

13. The method of claim 1, wherein an amount of Reb A released is greater than 30% of a total intracellular and an extracellular amount of Reb A produced during fermentation.

14. The method of claim 1, wherein an amount of Reb B released is greater than 30% of a total intracellular and an extracellular amount of Reb B produced during fermentation, can be released extracellularly in a range of about 25% to about 100% of the of the total amount of Reb B produced during the fermentation.

15. A composition, comprising a yeast host cell producing one or more steviol glycosides and one or more steviol glycosides that are released from the host cell by heating the composition to a temperature in a range from 50° C. to 95° C. for 5 minutes to 48 hours;
   wherein the extracellular nitrogen content in the composition after the heat treatment is not increased by more than 45% of the total extracellular and intracellular nitrogen content in the composition;
   wherein the extracellular phosphorous content in the composition after the heat treatment is not increased by more than 70% of the total extracellular and intracellular phosphorous content in the composition; and
   wherein the one or more steviol glycosides is rebaudioside M (Reb M), rebaudioside D (Reb D), rebaudioside A (Reb A), rebaudioside B (Reb B), or combinations thereof.

* * * * *

SEQUENCE LISTING

```
<160> NUMBER OF SEQ ID NOS: 22

<210> SEQ ID NO 1
<211> LENGTH: 460
<212> TYPE: PRT
<213> ORGANISM: Stevia rebaudiana

<400> SEQUENCE: 1

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110
```

```
Ala Ile Ile Tyr Asp Ser Met Thr Glu Trp Val Leu Asp Val Ala Ile
            115                 120                 125

Glu Phe Gly Ile Asp Gly Gly Ser Phe Phe Thr Gln Ala Cys Val Val
        130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
            210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
            290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
            370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460

<210> SEQ ID NO 2
<211> LENGTH: 481
<212> TYPE: PRT
<213> ORGANISM: Stevia rebaudiana

<400> SEQUENCE: 2

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
```

```
                    20                  25                  30
Leu Leu His His Lys Gly Leu Gln Ile Thr Phe Val Asn Thr Asp Phe
            35                  40                  45
Ile His Asn Gln Phe Leu Glu Ser Ser Gly Pro His Cys Leu Asp Gly
        50                  55                  60
Ala Pro Gly Phe Arg Phe Glu Thr Ile Pro Asp Gly Val Ser His Ser
65                  70                  75                  80
Pro Glu Ala Ser Ile Pro Ile Arg Glu Ser Leu Leu Arg Ser Ile Glu
                85                  90                  95
Thr Asn Phe Leu Asp Arg Phe Ile Asp Leu Val Thr Lys Leu Pro Asp
            100                 105                 110
Pro Pro Thr Cys Ile Ile Ser Asp Gly Phe Leu Ser Val Phe Thr Ile
        115                 120                 125
Asp Ala Ala Lys Lys Leu Gly Ile Pro Val Met Met Tyr Trp Thr Leu
        130                 135                 140
Ala Ala Cys Gly Phe Met Gly Phe Tyr His Ile His Ser Leu Ile Glu
145                 150                 155                 160
Lys Gly Phe Ala Pro Leu Lys Asp Ala Ser Tyr Leu Thr Asn Gly Tyr
                165                 170                 175
Leu Asp Thr Val Ile Asp Trp Val Pro Gly Met Glu Gly Ile Arg Leu
            180                 185                 190
Lys Asp Phe Pro Leu Asp Trp Ser Thr Asp Leu Asn Asp Lys Val Leu
        195                 200                 205
Met Phe Thr Thr Glu Ala Pro Gln Arg Ser His Lys Val Ser His His
        210                 215                 220
Ile Phe His Thr Phe Asp Glu Leu Glu Pro Ser Ile Ile Lys Thr Leu
225                 230                 235                 240
Ser Leu Arg Tyr Asn His Ile Tyr Thr Ile Gly Pro Leu Gln Leu Leu
                245                 250                 255
Leu Asp Gln Ile Pro Glu Glu Lys Lys Gln Thr Gly Ile Thr Ser Leu
            260                 265                 270
His Gly Tyr Ser Leu Val Lys Glu Glu Pro Glu Cys Phe Gln Trp Leu
        275                 280                 285
Gln Ser Lys Glu Pro Asn Ser Val Val Tyr Val Asn Phe Gly Ser Thr
        290                 295                 300
Thr Val Met Ser Leu Glu Asp Met Thr Glu Phe Gly Trp Gly Leu Ala
305                 310                 315                 320
Asn Ser Asn His Tyr Phe Leu Trp Ile Ile Arg Ser Asn Leu Val Ile
                325                 330                 335
Gly Glu Asn Ala Val Leu Pro Pro Glu Leu Glu Glu His Ile Lys Lys
            340                 345                 350
Arg Gly Phe Ile Ala Ser Trp Cys Ser Gln Glu Lys Val Leu Lys His
        355                 360                 365
Pro Ser Val Gly Gly Phe Leu Thr His Cys Gly Trp Gly Ser Thr Ile
        370                 375                 380
Glu Ser Leu Ser Ala Gly Val Pro Met Ile Cys Trp Pro Tyr Ser Trp
385                 390                 395                 400
Asp Gln Leu Thr Asn Cys Arg Tyr Ile Cys Lys Glu Trp Glu Val Gly
                405                 410                 415
Leu Glu Met Gly Thr Lys Val Lys Arg Asp Glu Val Lys Arg Leu Val
            420                 425                 430
Gln Glu Leu Met Gly Glu Gly Gly His Lys Met Arg Asn Lys Ala Lys
        435                 440                 445
```

```
Asp Trp Lys Glu Lys Ala Arg Ile Ala Ile Ala Pro Asn Gly Ser Ser
        450                 455                 460

Ser Leu Asn Ile Asp Lys Met Val Lys Glu Ile Thr Val Leu Ala Arg
465                 470                 475                 480

Asn

<210> SEQ ID NO 3
<211> LENGTH: 458
<212> TYPE: PRT
<213> ORGANISM: Stevia rebaudiana

<400> SEQUENCE: 3

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335
```

```
Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
                435                 440                 445

Glu Ser Leu Val Ser Tyr Ile Ser Ser Leu
        450                 455

<210> SEQ ID NO 4
<211> LENGTH: 473
<212> TYPE: PRT
<213> ORGANISM: Stevia rebaudiana

<400> SEQUENCE: 4

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
                20                  25                  30

Leu Ser Lys Leu Ile Ala Glu Lys Gly His Lys Val Ser Phe Leu Ser
                35                  40                  45

Thr Thr Arg Asn Ile Gln Arg Leu Ser Ser His Ile Ser Pro Leu Ile
        50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
                100                 105                 110

His Ser Pro Asp Trp Ile Ile Tyr Asp Tyr Thr His Tyr Trp Leu Pro
                115                 120                 125

Ser Ile Ala Ala Ser Leu Gly Ile Ser Arg Ala His Phe Ser Val Thr
        130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
                180                 185                 190

Ala Arg Leu Val Pro Tyr Lys Ala Pro Gly Ile Ser Asp Gly Tyr Arg
                195                 200                 205

Met Gly Met Val Leu Lys Gly Ser Asp Cys Leu Leu Ser Lys Cys Tyr
        210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
```

|     |     |     |     |     | 245 |     |     |     | 250 |     |     |     |     | 255 |
| --- | --- | --- | --- | --- | --- | --- | --- | --- | --- | --- | --- | --- | --- | --- |
| Glu | Lys | Asp | Glu | Thr | Trp | Val | Ser | Ile | Lys | Lys | Trp | Leu | Asp | Gly | Lys |
|     |     |     | 260 |     |     |     | 265 |     |     |     | 270 |     |     |     |     |

Gln Lys Gly Ser Val Val Tyr Val Ala Leu Gly Ser Glu Ala Leu Val
    275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
                340                 345                 350

Glu Ser Val Cys Gly Phe Leu Thr His Cys Ser Gly Ser Ile Val
                355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Asp Gly Cys Leu Thr Lys Glu Ser Val
                405                 410                 415

Ala Arg Ser Leu Arg Ser Val Val Glu Lys Glu Gly Glu Ile Tyr
                420                 425                 430

Lys Ala Asn Ala Arg Glu Leu Ser Lys Ile Tyr Asn Asp Thr Lys Val
                435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 5
<211> LENGTH: 1422
<212> TYPE: DNA
<213> ORGANISM: Artificial Sequence
<220> FEATURE:
<223> OTHER INFORMATION: Synthetic oligonucleotide

<400> SEQUENCE: 5
atggctactt ctgattccat cgttgacgat agaaagcaat tgcatgttgc tacttttcca      60
tggttggctt tcggtcatat tttgccatac ttgcaattgt ccaagttgat tgctgaaaag     120
ggtcacaagg tttcattctt gtctaccacc agaaacatcc aaagattgtc ctctcatatc     180
tccccattga tcaacgttgt tcaattgact ttgccaagag tccaagaatt gccagaagat     240
gctgaagcta ctactgatgt tcatccagaa gatatccctt acttgaaaaa ggcttccgat     300
ggtttacaac agaagttac tagattcttg aacaacatt ccccagattg gatcatctac       360
gattatactc attactggtt gccatccatt gctgcttcat gggtatttc tagagcccat      420 ttctctgtta ctactccatg ggctattgct tatatgggtc catctgctga tgctatgatt     480
aacggttctg atggtagaac taccgttgaa gatttgacta ctccaccaaa gtggtttcca     540
tttccaacaa aagtctgttg gagaaaacac gatttggcta gattggttcc atacaaagct     600
ccaggtattt ctgatggtta cagaatgggt atggttttga aggttccga ttgcttgttg      660 tctaagtgct atcatgaatt cggtactcaa tggttgcctt tgttggaaac attgcatcaa     720
gttccagttg ttccagtagg tttgttgcca ccagaaattc aggtgacga aaaagacgaa      780

```
acttgggttt ccatcaaaaa gtggttggat ggtaagcaaa agggttctgt tgtttatgtt    840
gctttgggtt ccgaagcttt ggtttctcaa accgaagttg ttgaattggc tttgggtttg    900
gaattgtctg gtttgccatt tgtttgggct tacagaaaac ctaaaggtcc agctaagtct    960
gattctgttg aattgccaga tggtttcgtt gaaagaacta gagatagagg tttggtttgg   1020
acttcttggg ctccacaatt gagaattttg tctcatgaat ccgtctgtgg tttcttgact   1080
cattgtggtt ctggttctat cgttgaaggt ttgatgtttg gtcacccatt gattatgttg   1140
ccaatctttg gtgaccaacc attgaacgct agattattgg aagataagca agtcggtatc   1200
gaaatcccaa gaaatgaaga gatggttgc ttgaccaaag aatctgttgc tagatctttg   1260
agatccgttg tcgttgaaaa agaaggtgaa atctacaagg ctaacgctag agaattgtcc   1320
aagatctaca acgataccaa ggtcgaaaaa gaatacgttt cccaattcgt tgactacttg   1380
gaaaagaatg ctagagctgt tgccattgat catgaatctt ga                      1422
```

<210> SEQ ID NO 6
<211> LENGTH: 297
<212> TYPE: PRT
<213> ORGANISM: Synechococcus sp.

<400> SEQUENCE: 6

```
Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255
```

-continued

Leu Glu Ala Ser Arg Gln Lys Ala Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295

<210> SEQ ID NO 7
<211> LENGTH: 827
<212> TYPE: PRT
<213> ORGANISM: Zea mays

<400> SEQUENCE: 7

Met Val Leu Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Gly Arg Trp Arg Arg Ala Leu
        35                  40                  45

Ala Arg Ala Gln His Thr Ser Glu Ser Ala Ala Val Ala Lys Gly Ser
    50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
                100                 105                 110

Asp Thr Ala Trp Val Gly Leu Val Pro Arg Leu Asp Gly Gly Glu Gly
            115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
            180                 185                 190

Lys Leu Ala Thr Glu Asp Glu Glu Ser Met Pro Ile Gly Phe Glu Leu
    195                 200                 205

Ala Phe Pro Ser Leu Ile Glu Leu Ala Lys Ser Leu Gly Val His Asp
210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
            260                 265                 270

Leu Leu Lys Leu Gln Ser Ser Asp Gly Ser Phe Leu Phe Ser Pro Ala
    275                 280                 285

Ala Thr Ala Tyr Ala Leu Met Asn Thr Gly Asp Asp Arg Cys Phe Ser
290                 295                 300

Tyr Ile Asp Arg Thr Val Lys Lys Phe Asn Gly Gly Val Pro Asn Val
305                 310                 315                 320

Tyr Pro Val Asp Leu Phe Glu His Ile Trp Ala Val Asp Arg Leu Glu
                325                 330                 335

```
Arg Leu Gly Ile Ser Arg Tyr Phe Gln Lys Glu Ile Glu Gln Cys Met
                340                 345                 350

Asp Tyr Val Asn Arg His Trp Thr Glu Asp Gly Ile Cys Trp Ala Arg
            355                 360                 365

Asn Ser Asp Val Lys Glu Val Asp Asp Thr Ala Met Ala Phe Arg Leu
        370                 375                 380

Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
                405                 410                 415

Val Thr Gly Met Tyr Asn Leu Asn Arg Ala Ser Gln Ile Ser Phe Pro
            420                 425                 430

Gly Glu Asp Val Leu His Arg Ala Gly Ala Phe Ser Tyr Glu Phe Leu
        435                 440                 445

Arg Arg Lys Glu Ala Glu Gly Ala Leu Arg Asp Lys Trp Ile Ile Ser
450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
        515                 520                 525

Cys Gln Ala Leu His Gln Leu Glu Trp Gln Gly Leu Lys Arg Trp Tyr
530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ser Val Tyr Glu Pro Cys Arg Ala
                565                 570                 575

Ala Glu Arg Leu Ala Trp Ala Arg Ala Ala Ile Leu Ala Asn Ala Val
            580                 585                 590

Ser Thr His Leu Arg Asn Ser Pro Ser Phe Arg Glu Arg Leu Glu His
        595                 600                 605

Ser Leu Arg Cys Arg Pro Ser Glu Glu Thr Asp Gly Ser Trp Phe Asn
610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
                645                 650                 655

Glu Asp Ile Ile His Lys Leu Leu Arg Ser Ala Trp Ala Glu Trp Val
            660                 665                 670

Arg Glu Lys Ala Asp Ala Ala Asp Ser Val Cys Asn Gly Ser Ser Ala
        675                 680                 685

Val Glu Gln Glu Gly Ser Arg Met Val His Asp Lys Gln Thr Cys Leu
690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750
```

```
Lys Asn Glu Met Met Ser His Val Asp Asp Glu Leu Lys Leu Arg
            755                 760                 765
Ile Arg Glu Phe Val Gln Tyr Leu Leu Arg Leu Gly Glu Lys Lys Thr
770                 775                 780
Gly Ser Ser Glu Thr Arg Gln Thr Phe Leu Ser Ile Val Lys Ser Cys
785                 790                 795                 800
Tyr Tyr Ala Ala His Cys Pro Pro His Val Val Asp Arg His Ile Ser
                805                 810                 815
Arg Val Ile Phe Glu Pro Val Ser Ala Ala Lys
            820                 825

<210> SEQ ID NO 8
<211> LENGTH: 785
<212> TYPE: PRT
<213> ORGANISM: Arabidopsis thaliana

<400> SEQUENCE: 8

Met Ser Ile Asn Leu Arg Ser Ser Gly Cys Ser Ser Pro Ile Ser Ala
1               5                   10                  15
Thr Leu Glu Arg Gly Leu Asp Ser Glu Val Gln Thr Arg Ala Asn Asn
            20                  25                  30
Val Ser Phe Glu Gln Thr Lys Glu Lys Ile Arg Lys Met Leu Glu Lys
        35                  40                  45
Val Glu Leu Ser Val Ser Ala Tyr Asp Thr Ser Trp Val Ala Met Val
    50                  55                  60
Pro Ser Pro Ser Ser Gln Asn Ala Pro Leu Phe Pro Gln Cys Val Lys
65                  70                  75                  80
Trp Leu Leu Asp Asn Gln His Glu Asp Gly Ser Trp Gly Leu Asp Asn
                85                  90                  95
His Asp His Gln Ser Leu Lys Lys Asp Val Leu Ser Ser Thr Leu Ala
            100                 105                 110
Ser Ile Leu Ala Leu Lys Lys Trp Gly Ile Gly Glu Arg Gln Ile Asn
        115                 120                 125
Lys Gly Leu Gln Phe Ile Glu Leu Asn Ser Ala Leu Val Thr Asp Glu
    130                 135                 140
Thr Ile Gln Lys Pro Thr Gly Phe Asp Ile Ile Phe Pro Gly Met Ile
145                 150                 155                 160
Lys Tyr Ala Arg Asp Leu Asn Leu Thr Ile Pro Leu Gly Ser Glu Val
                165                 170                 175
Val Asp Asp Met Ile Arg Lys Arg Asp Leu Asp Leu Lys Cys Asp Ser
            180                 185                 190
Glu Lys Phe Ser Lys Gly Arg Glu Ala Tyr Leu Ala Tyr Val Leu Glu
        195                 200                 205
Gly Thr Arg Asn Leu Lys Asp Trp Asp Leu Ile Val Lys Tyr Gln Arg
    210                 215                 220
Lys Asn Gly Ser Leu Phe Asp Ser Pro Ala Thr Thr Ala Ala Ala Phe
225                 230                 235                 240
Thr Gln Phe Gly Asn Asp Gly Cys Leu Arg Tyr Leu Cys Ser Leu Leu
                245                 250                 255
Gln Lys Phe Glu Ala Ala Val Pro Ser Val Tyr Pro Phe Asp Gln Tyr
            260                 265                 270
Ala Arg Leu Ser Ile Ile Val Thr Leu Glu Ser Leu Gly Ile Asp Arg
        275                 280                 285
Asp Phe Lys Thr Glu Ile Lys Ser Ile Leu Asp Glu Thr Tyr Arg Tyr
    290                 295                 300
```

```
Trp Leu Arg Gly Asp Glu Glu Ile Cys Leu Asp Leu Ala Thr Cys Ala
305                 310                 315                 320

Leu Ala Phe Arg Leu Leu Ala His Gly Tyr Asp Val Ser Tyr Asp
            325                 330                 335

Pro Leu Lys Pro Phe Ala Glu Glu Ser Gly Phe Ser Thr Leu Glu
            340                 345                 350

Gly Tyr Val Lys Asn Thr Phe Ser Val Leu Glu Leu Phe Lys Ala Ala
                355                 360                 365

Gln Ser Tyr Pro His Glu Ser Ala Leu Lys Lys Gln Cys Cys Trp Thr
370                 375                 380

Lys Gln Tyr Leu Glu Met Glu Leu Ser Ser Trp Val Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Lys Ile Leu Asn
            420                 425                 430

Gly Ser Ala Val Glu Asn Thr Arg Val Thr Lys Thr Ser Tyr Arg Leu
            435                 440                 445

His Asn Ile Cys Thr Ser Asp Ile Leu Lys Leu Ala Val Asp Asp Phe
450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
            515                 520                 525

Val Val Asp Asp Phe Phe Asp Val Gly Gly Ser Lys Glu Glu Leu Glu
530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
            595                 600                 605

Arg Glu Ala Glu Trp Ser Ser Asp Lys Ser Thr Pro Ser Leu Glu Asp
610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
            675                 680                 685

Leu Asn Ala Val Ser Leu His Met Lys His Glu Arg Asp Asn Arg Ser
690                 695                 700

Lys Glu Val Ile Ile Glu Ser Met Lys Gly Leu Ala Glu Arg Lys Arg
705                 710                 715                 720
```

Glu Glu Leu His Lys Leu Val Leu Glu Glu Lys Gly Ser Val Val Pro
              725                 730                 735

Arg Glu Cys Lys Glu Ala Phe Leu Lys Met Ser Lys Val Leu Asn Leu
          740                 745                 750

Phe Tyr Arg Lys Asp Asp Gly Phe Thr Ser Asn Asp Leu Met Ser Leu
      755                 760                 765

Val Lys Ser Val Ile Tyr Glu Pro Val Ser Leu Gln Lys Glu Ser Leu
  770                 775                 780

Thr
785

<210> SEQ ID NO 9
<211> LENGTH: 1542
<212> TYPE: DNA
<213> ORGANISM: Artificial Sequence
<220> FEATURE:
<223> OTHER INFORMATION: Codon-optimized KO

<400> SEQUENCE: 9

```
atggatgctg tgacgggttt gttaactgtc ccagcaaccg ctataactat tggtggaact      60
gctgtagcat tggcggtagc gctaatcttt tggtacctga atcctacaca atcagctaga     120
agatcccaat caaatcatct tccaagagtg cctgaagtcc aggtgttcc attgttagga      180
aatctgttac aattgaagga gaaaaagcca tacatgactt ttacgagatg ggcagcgaca     240
tatggaccta tctatagtat caaaactggg gctacaagta tggttgtggt atcatctaat     300
gagatagcca aggaggcatt ggtgaccaga ttccaatcca tatctacaag gaacttatct     360
aaagccctga agtacttac agcagataag acaatggtcg caatgtcaga ttatgatgat     420
tatcataaaa cagttaagag acacatactg accgccgtct tgggtcctaa tgcacagaaa     480
aagcatagaa ttcacagaga tatcatgatg gataacatat ctactcaact tcatgaattc     540
gtgaaaaaca acccagaaca ggaagaggta gaccttagaa aaatctttca atctgagtta     600
ttcggcttag ctatgagaca agccttagga aaggatgttg aaagtttgta cgttgaagac     660
ctgaaaatca ctatgaatag agacgaaatc tttcaagtcc ttgttgttga tccaatgatg     720
ggagcaatcg atgttgattg gagagacttc tttccatacc taaagtgggt cccaaacaaa     780
aagttcgaaa atactattca acaaatgtac atcagaagag aagctgttat gaaatcttta     840
atcaaagagc acaaaagagg aatagcgtca ggcgaaaagc taaatagtta tatcgattac     900
cttttatctg aagctcaaac tttaaccgat cagcaactat tgatgtcctt gtgggaacca     960
atcattgaat cttcagatac aacaatggtc acaacagaat gggcaatgta cgaattagct    1020
aaaaacccta aattgcaaga taggttgtac agagacatta agtccgtctg tggatctgaa    1080
aagataaccg aagagcatct atcacagctg ccttacatta agctatttt ccacgaaaca    1140
ctgagaagac actcaccagt tcctatcatt cctctaagac atgtacatga agataccgtt    1200
ctaggcggct accatgttcc tgctggcaca gaacttgccg ttaacatcta cggttgcaac    1260
atggacaaaa acgtttggga aaatccagag gaatggaacc agaaagatt catgaaagag    1320
aatgagacaa ttgatttca aaagacgatg gccttcggtg gtggtaagag agtttgtgct    1380
ggttccttgc aagcccttt aactgcatct attgggattg ggagaatggt tcaagagttc    1440
gaatggaaac tgaaggatat gactcaagag gaagtgaaca cgataggcct aactacacaa    1500
atgttaagac cattgagagc tattatcaaa cctaggatct aa                       1542
```

<210> SEQ ID NO 10

<211> LENGTH: 513
<212> TYPE: PRT
<213> ORGANISM: Stevia rebaudiana

<400> SEQUENCE: 10

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val

```
                385                 390                 395                 400
Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
                500                 505                 510

Ile
```

<210> SEQ ID NO 11
<211> LENGTH: 2139
<212> TYPE: DNA
<213> ORGANISM: Arabidopsis thaliana

<400> SEQUENCE: 11

```
atgtcttcct cttcctcttc cagtacctct atgattgatt tgatggctgc tattattaaa      60
ggtgaaccag ttatcgtctc cgacccagca aatgcctctg cttatgaatc agttgctgca     120
gaattgtctt caatgttgat cgaaaacaga caattcgcca tgatcgtaac tacatcaatc     180
gctgttttga tcggttgtat tgtcatgttg gtatggagaa gatccggtag tggtaattct     240
aaaagagtcg aacctttgaa accattagta attaagccaa gagaagaaga aatagatgac     300
ggtagaaaga agttacaat attttttcggt acccaaactg gtacagctga aggttttgca     360
aaagccttag gtgaagaagc taaggcaaga tacgaaaaga ctagattcaa gatagtcgat     420
ttggatgact atgccgctga tgacgatgaa tacgaagaaa agttgaagaa agaagatgtt     480
gcatttttct ttttggcaac ctatggtgac ggtgaaccaa ctgacaatgc agccagattc     540
tacaaatggt ttacagaggg taatgatcgt ggtgaatggt tgaaaaactt aaagtacggt     600
gttttcggtt tgggtaacag acaatacgaa catttcaaca aagttgcaaa ggttgtcgac     660
gatatttggg tcgaacaagg tgctcaaaga ttagtccaag taggtttggg tgacgatgac     720
caatgtatag aagatgactt tactgcctgg agagaagctt gtggcctga attagacaca     780 atcttgagag aagaaggtga caccgccgtt gctaccccat atactgctgc agtattagaa     840
tacagagttt ccatccatga tagtgaagac gcaaagttta atgatatcac tttggccaat     900
ggtaacggtt atacagtttt cgatgcacaa cacccttaca agctaacgt tgcagtcaag     960 agagaattac atacaccaga tccgacaga agttgtatac acttggaatt tgatatcgct    1020
ggttccggtt aaccatgaa gttgggtgac catgtaggtg ttttatgcga caatttgtct    1080
gaaactgttg atgaagcatt gagattgttg gatatgtccc ctgacactta ttttagtttg    1140
cacgctgaaa agaagatgg tacaccaatt ccagttctt taccacctcc attccctcca    1200
tgtaacttaa gaacagcctt gaccagatac gcttgcttgt tatcatcccc taaaaagtcc    1260
gccttggttg cttagccgc tcatgctagt gatcctactg aagcagaaag attgaaacac    1320
ttagcatctc cagccggtaa agatgaatat tcaaagtggg tagttgaatc tcaaagatca    1380
```

```
ttgttagaag ttatggcaga atttccatct gccaagcctc cattaggtgt cttctttgct    1440
ggtgtagcac ctagattgca accaagattc tactcaatca gttcttcacc taagatcgct    1500
gaaactagaa ttcatgttac atgtgcatta gtctacgaaa agatgccaac cggtagaatt    1560
cacaagggtg tatgctctac ttggatgaaa aatgctgttc cttacgaaaa atcagaaaag    1620
ttgttcttag gtagaccaat cttcgtaaga caatcaaact tcaagttgcc ttctgattca    1680
aaggttccaa taatcatgat aggtcctggt acaggtttag ccccattcag aggtttcttg    1740
caagaaagat tggctttagt tgaatctggt gtcgaattag gtccttcagt tttgttcttt    1800
ggttgtagaa acagaagaat ggatttcatc tatgaagaag aattgcaaag attcgtcgaa    1860
tctggtgcat tggccgaatt atctgtagct tttcaagag aaggtccaac taaggaatac    1920
gttcaacata agatgatgga taaggcatcc gacatatgga acatgatcag tcaaggtgct    1980
tatttgtacg tttgcggtga cgcaaagggt atggccagag atgtccatag atctttgcac    2040
acaattgctc aagaacaagg ttccatggat agtaccaaag ctgaaggttt cgtaaagaac    2100
ttacaaactt ccggtagata cttgagagat gtctggtga                           2139
```

<210> SEQ ID NO 12
<211> LENGTH: 712
<212> TYPE: PRT
<213> ORGANISM: Arabidopsis thaliana

<400> SEQUENCE: 12

```
Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240
```

```
Gln Cys Ile Glu Asp Asp Phe Thr Ala Trp Arg Glu Ala Leu Trp Pro
                245                 250                 255
Glu Leu Asp Thr Ile Leu Arg Glu Gly Asp Thr Ala Val Ala Thr
            260                 265                 270
Pro Tyr Thr Ala Ala Val Leu Glu Tyr Arg Val Ser Ile His Asp Ser
            275                 280                 285
Glu Asp Ala Lys Phe Asn Asp Ile Thr Leu Ala Asn Gly Asn Gly Tyr
            290                 295                 300
Thr Val Phe Asp Ala Gln His Pro Tyr Lys Ala Asn Val Ala Val Lys
305                 310                 315                 320
Arg Glu Leu His Thr Pro Glu Ser Asp Arg Ser Cys Ile His Leu Glu
                325                 330                 335
Phe Asp Ile Ala Gly Ser Gly Leu Thr Met Lys Leu Gly Asp His Val
                340                 345                 350
Gly Val Leu Cys Asp Asn Leu Ser Glu Thr Val Asp Glu Ala Leu Arg
            355                 360                 365
Leu Leu Asp Met Ser Pro Asp Thr Tyr Phe Ser Leu His Ala Glu Lys
            370                 375                 380
Glu Asp Gly Thr Pro Ile Ser Ser Ser Leu Pro Pro Phe Pro Pro
385                 390                 395                 400
Cys Asn Leu Arg Thr Ala Leu Thr Arg Tyr Ala Cys Leu Leu Ser Ser
                405                 410                 415
Pro Lys Lys Ser Ala Leu Val Ala Leu Ala Ala His Ala Ser Asp Pro
                420                 425                 430
Thr Glu Ala Glu Arg Leu Lys His Leu Ala Ser Pro Ala Gly Lys Asp
            435                 440                 445
Glu Tyr Ser Lys Trp Val Val Glu Ser Gln Arg Ser Leu Leu Glu Val
            450                 455                 460
Met Ala Glu Phe Pro Ser Ala Lys Pro Pro Leu Gly Val Phe Phe Ala
465                 470                 475                 480
Gly Val Ala Pro Arg Leu Gln Pro Arg Phe Tyr Ser Ile Ser Ser Ser
                485                 490                 495
Pro Lys Ile Ala Glu Thr Arg Ile His Val Thr Cys Ala Leu Val Tyr
                500                 505                 510
Glu Lys Met Pro Thr Gly Arg Ile His Lys Gly Val Cys Ser Thr Trp
            515                 520                 525
Met Lys Asn Ala Val Pro Tyr Glu Lys Ser Glu Lys Leu Phe Leu Gly
            530                 535                 540
Arg Pro Ile Phe Val Arg Gln Ser Asn Phe Lys Leu Pro Ser Asp Ser
545                 550                 555                 560
Lys Val Pro Ile Ile Met Ile Gly Pro Gly Thr Gly Leu Ala Pro Phe
                565                 570                 575
Arg Gly Phe Leu Gln Glu Arg Leu Ala Leu Val Glu Ser Gly Val Glu
            580                 585                 590
Leu Gly Pro Ser Val Leu Phe Phe Gly Cys Arg Asn Arg Arg Met Asp
            595                 600                 605
Phe Ile Tyr Glu Glu Glu Leu Gln Arg Phe Val Glu Ser Gly Ala Leu
            610                 615                 620
Ala Glu Leu Ser Val Ala Phe Ser Arg Glu Gly Pro Thr Lys Glu Tyr
625                 630                 635                 640
Val Gln His Lys Met Met Asp Lys Ala Ser Asp Ile Trp Asn Met Ile
                645                 650                 655
Ser Gln Gly Ala Tyr Leu Tyr Val Cys Gly Asp Ala Lys Gly Met Ala
```

```
                660             665             670
Arg Asp Val His Arg Ser Leu His Thr Ile Ala Gln Glu Gln Gly Ser
            675             680             685

Met Asp Ser Thr Lys Ala Glu Gly Phe Val Lys Asn Leu Gln Thr Ser
690             695             700

Gly Arg Tyr Leu Arg Asp Val Trp
705             710

<210> SEQ ID NO 13
<211> LENGTH: 462
<212> TYPE: PRT
<213> ORGANISM: Oryza sativa

<400> SEQUENCE: 13

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305                 310                 315                 320
```

```
Leu Pro Ala Gly Phe Glu Glu Arg Thr Arg Gly Arg Gly Val Val Ala
                325                 330                 335
Thr Arg Trp Val Pro Gln Met Ser Ile Leu Ala His Ala Ala Val Gly
            340                 345                 350
Ala Phe Leu Thr His Cys Gly Trp Asn Ser Thr Ile Glu Gly Leu Met
        355                 360                 365
Phe Gly His Pro Leu Ile Met Leu Pro Ile Phe Gly Asp Gln Gly Pro
    370                 375                 380
Asn Ala Arg Leu Ile Glu Ala Lys Asn Ala Gly Leu Gln Val Ala Arg
385                 390                 395                 400
Asn Asp Gly Asp Gly Ser Phe Asp Arg Glu Gly Val Ala Ala Ala Ile
                405                 410                 415
Arg Ala Val Ala Val Glu Glu Glu Ser Ser Lys Val Phe Gln Ala Lys
            420                 425                 430
Ala Lys Lys Leu Gln Glu Ile Val Ala Asp Met Ala Cys His Glu Arg
        435                 440                 445
Tyr Ile Asp Gly Phe Ile Gln Gln Leu Arg Ser Tyr Lys Asp
    450                 455                 460

<210> SEQ ID NO 14
<211> LENGTH: 1503
<212> TYPE: DNA
<213> ORGANISM: Artificial Sequence
<220> FEATURE:
<223> OTHER INFORMATION: Codon-optimized stevia rebaudiana

<400> SEQUENCE: 14
atggaagcct cttacctata catttctatt ttgcttttac tggcatcata cctgttcacc      60
actcaactta aaggaagag cgctaatcta ccaccaaccg tgtttccatc aataccaatc     120
attggacact tatacttact caaaaagcct ctttatagaa ctttagcaaa aattgccgct     180
aagtacggac caatactgca attacaactc ggctacagac gtgttctggt gatttcctca     240
ccatcagcag cagaagagtg ctttaccaat aacgatgtaa tcttcgcaaa tagacctaag     300
acattgtttg gcaaaatagt gggtggaaca tcccttggca gtttatccta cggcgatcaa     360
tggcgtaatc taaggagagt agcttctatc gaaatcctat cagttcatag gttgaacgaa     420
tttcatgata tcagagtgga tgagaacaga ttgttaatta gaaaacttag aagttcatct     480
tctcctgtta ctcttataac agtcttttat gctctaacat gaacgtcat tatgagaatg     540 atctctggca aagatatttt cgacagtggg gatagagaat ggaggagga aggtaagaga     600 tttcgagaaa tcttagacga aacgttgctt ctagccggtg cttctaatgt tggcgactac     660
ttaccaatat tgaactggtt gggagttaag tctcttgaaa agaaattgat cgctttgcag     720
aaaaagagag atgactttt ccagggtttg attgaacagg ttagaaaatc tcgtggtgct     780
aaagtaggca aaggtagaaa aacgatgatc gaactcttat tatctttgca agagtcagaa     840
cctgagtact atacagatgc tatgataaga tcttttgtcc taggtctgct ggctgcaggt     900
agtgatactt cagcgggcac tatggaatgg gccatgagct actggtcaa tcacccacat     960 gtattgaaga agctcaagc tgaaatcgat agagttatcg gtaataacag attgattgac    1020
gagtcagaca ttggaaatat cccttacatc gggtgtatta tcaatgaaac tctaagactc    1080
tatccagcag ggccattgtt gttcccacat gaaagttctg ccgactgcgt tatttccggt    1140
tacaatatac ctagaggtac aatgttaatc gtaaaccaat gggcgattca tcacgatcct    1200
aaagtctggg atgatcctga aaccctttaaa cctgaaagat ttcaaggatt agaaggaact    1260
```

-continued

```
agagatggtt tcaaacttat gccattcggt tctgggagaa gaggatgtcc aggtgaaggt      1320
ttggcaataa ggctgttagg gatgacacta ggctcagtga tccaatgttt tgattgggag      1380
agagtaggag atgagatggt tgacatgaca gaaggtttgg gtgtcacact tcctaaggcc      1440
gttccattag ttgccaaatg taagccacgt tccgaaatga ctaatctcct atccgaactt      1500
taa                                                                   1503
```

<210> SEQ ID NO 15
<211> LENGTH: 500
<212> TYPE: PRT
<213> ORGANISM: Stevia rebaudiana

<400> SEQUENCE: 15

| | | | | | | | | | | | | | | |
|---|---|---|---|---|---|---|---|---|---|---|---|---|---|---|
| Met | Glu | Ala | Ser | Tyr | Leu | Tyr | Ile | Ser | Ile | Leu | Leu | Leu | Ala | Ser |
| 1 | | | | 5 | | | | | 10 | | | | | 15 |
| Tyr | Leu | Phe | Thr | Thr | Gln | Leu | Arg | Arg | Lys | Ser | Ala | Asn | Leu | Pro | Pro |
| | | | 20 | | | | | 25 | | | | | 30 | | |
| Thr | Val | Phe | Pro | Ser | Ile | Pro | Ile | Ile | Gly | His | Leu | Tyr | Leu | Leu | Lys |
| | | 35 | | | | | 40 | | | | | 45 | | | |
| Lys | Pro | Leu | Tyr | Arg | Thr | Leu | Ala | Lys | Ile | Ala | Ala | Lys | Tyr | Gly | Pro |
| | 50 | | | | | 55 | | | | | 60 | | | | |
| Ile | Leu | Gln | Leu | Gln | Leu | Gly | Tyr | Arg | Arg | Val | Leu | Val | Ile | Ser | Ser |
| 65 | | | | | 70 | | | | | 75 | | | | | 80 |
| Pro | Ser | Ala | Ala | Glu | Glu | Cys | Phe | Thr | Asn | Asn | Asp | Val | Ile | Phe | Ala |
| | | | | 85 | | | | | 90 | | | | | 95 | |
| Asn | Arg | Pro | Lys | Thr | Leu | Phe | Gly | Lys | Ile | Val | Gly | Gly | Thr | Ser | Leu |
| | | | 100 | | | | | 105 | | | | | 110 | | |
| Gly | Ser | Leu | Ser | Tyr | Gly | Asp | Gln | Trp | Arg | Asn | Leu | Arg | Arg | Val | Ala |
| | | 115 | | | | | 120 | | | | | 125 | | | |
| Ser | Ile | Glu | Ile | Leu | Ser | Val | His | Arg | Leu | Asn | Glu | Phe | His | Asp | Ile |
| | 130 | | | | | 135 | | | | | 140 | | | | |
| Arg | Val | Asp | Glu | Asn | Arg | Leu | Leu | Ile | Arg | Lys | Leu | Arg | Ser | Ser | Ser |
| 145 | | | | | 150 | | | | | 155 | | | | | 160 |
| Ser | Pro | Val | Thr | Leu | Ile | Thr | Val | Phe | Tyr | Ala | Leu | Thr | Leu | Asn | Val |
| | | | | 165 | | | | | 170 | | | | | 175 | |
| Ile | Met | Arg | Met | Ile | Ser | Gly | Lys | Arg | Tyr | Phe | Asp | Ser | Gly | Asp | Arg |
| | | | 180 | | | | | 185 | | | | | 190 | | |
| Glu | Leu | Glu | Glu | Gly | Lys | Arg | Phe | Arg | Glu | Ile | Leu | Asp | Glu | Thr |
| | | 195 | | | | | 200 | | | | | 205 | | | |
| Leu | Leu | Leu | Ala | Gly | Ala | Ser | Asn | Val | Gly | Asp | Tyr | Leu | Pro | Ile | Leu |
| | 210 | | | | | 215 | | | | | 220 | | | | |
| Asn | Trp | Leu | Gly | Val | Lys | Ser | Leu | Glu | Lys | Lys | Leu | Ile | Ala | Leu | Gln |
| 225 | | | | | 230 | | | | | 235 | | | | | 240 |
| Lys | Lys | Arg | Asp | Asp | Phe | Phe | Gln | Gly | Leu | Ile | Glu | Gln | Val | Arg | Lys |
| | | | | 245 | | | | | 250 | | | | | 255 | |
| Ser | Arg | Gly | Ala | Lys | Val | Gly | Lys | Gly | Arg | Lys | Thr | Met | Ile | Glu | Leu |
| | | | 260 | | | | | 265 | | | | | 270 | | |
| Leu | Leu | Ser | Leu | Gln | Glu | Ser | Glu | Pro | Glu | Tyr | Tyr | Thr | Asp | Ala | Met |
| | | 275 | | | | | 280 | | | | | 285 | | | |
| Ile | Arg | Ser | Phe | Val | Leu | Gly | Leu | Leu | Ala | Ala | Gly | Ser | Asp | Thr | Ser |
| | 290 | | | | | 295 | | | | | 300 | | | | |
| Ala | Gly | Thr | Met | Glu | Trp | Ala | Met | Ser | Leu | Leu | Val | Asn | His | Pro | His |
| 305 | | | | | 310 | | | | | 315 | | | | | 320 |
| Val | Leu | Lys | Lys | Ala | Gln | Ala | Glu | Ile | Asp | Arg | Val | Ile | Gly | Asn | Asn |

```
                325                 330                 335
Arg Leu Ile Asp Glu Ser Asp Ile Gly Asn Ile Pro Tyr Ile Gly Cys
            340                 345                 350
Ile Ile Asn Glu Thr Leu Arg Leu Tyr Pro Ala Gly Pro Leu Leu Phe
            355                 360                 365
Pro His Glu Ser Ser Ala Asp Cys Val Ile Ser Gly Tyr Asn Ile Pro
            370                 375                 380
Arg Gly Thr Met Leu Ile Val Asn Gln Trp Ala Ile His His Asp Pro
385                 390                 395                 400
Lys Val Trp Asp Asp Pro Glu Thr Phe Lys Pro Glu Arg Phe Gln Gly
                405                 410                 415
Leu Glu Gly Thr Arg Asp Gly Phe Lys Leu Met Pro Phe Gly Ser Gly
                420                 425                 430
Arg Arg Gly Cys Pro Gly Glu Gly Leu Ala Ile Arg Leu Leu Gly Met
                435                 440                 445
Thr Leu Gly Ser Val Ile Gln Cys Phe Asp Trp Glu Arg Val Gly Asp
            450                 455                 460
Glu Met Val Asp Met Thr Glu Gly Leu Gly Val Thr Leu Pro Lys Ala
465                 470                 475                 480
Val Pro Leu Val Ala Lys Cys Lys Pro Arg Ser Glu Met Thr Asn Leu
                485                 490                 495
Leu Ser Glu Leu
            500

<210> SEQ ID NO 16
<211> LENGTH: 2124
<212> TYPE: DNA
<213> ORGANISM: Stevia rebaudiana

<400> SEQUENCE: 16
atgcaatcta actccgtgaa gatttcgccg cttgatctgg taactgcgct gtttagcggc      60
aaggttttgg acacatcgaa cgcatcggaa tcgggagaat ctgctatgct gccgactata     120
gcgatgatta tggagaatcg tgagctgttg atgatactca aacgtcggt tgctgtattg     180 atcggatgcg ttgtcgtttt ggtgtggcgg agatcgtcta cgaagaagtc ggcgttggag     240
ccaccggtga ttgtggttcc gaagagagtg caagaggagg aagttgatga tggtaagaag     300
aaagttacgg ttttcttcgg cacccaaact ggaacagctg aaggcttcgc taaggcactt     360
gttgaggaag ctaaagctcg atatgaaaag gctgtcttta agtaattga tttggatgat     420 tatgctgctg atgacgatga gtatgaggag aaactaaaga aagaatcttt ggccttttc      480 tttttggcta cgtatggaga tggtgagcca acagataatg ctgccagatt ttataaatgg     540
tttactgagg gagatgcgaa aggagaatgg cttaataagc ttcaatatgg agtatttggt     600
ttgggtaaca gacaatatga acattttaac aagatcgcaa agtggttga tgatggtctt     660 gtagaacagg gtgcaaagcg tcttgttcct gttggacttg agatgatga tcaatgtatt     720 gaagatgact tcaccgcatg gaaagagtta gtatggccgg agttggatca attacttcgt     780
gatgaggatg acacaactgt tgctactcca tacacagctg ctgttgcaga atatcgcgtt     840 gttttttcatg aaaaaccaga cgcgcttct gaagattata gttatacaaa tggccatgct     900
gttcatgatg ctcaacatcc atgcagatcc aacgtggctg tcaaaaagga acttcatagt     960
cctgaatctg accggtcttg cactcatctt gaatttgaca tctcgaacac cggactatca    1020
tatgaaactg ggaccatgt tggagtttac tgtgaaaact tgagtgaagt tgtgaatgat    1080
```

-continued

```
gctgaaagat tagtaggatt accaccagac acttactcct ccatccacac tgatagtgaa    1140
gacgggtcgc cacttggcgg agcctcattg ccgcctcctt tcccgccatg cactttaagg    1200
aaagcattga cgtgttatgc tgatgttttg agttctccca agaagtcggc tttgcttgca    1260
ctagctgctc atgccaccga tcccagtgaa gctgatagat tgaaatttct tgcatccccc    1320
gccggaaagg atgaatattc tcaatggata gttgcaagcc aaagaagtct ccttgaagtc    1380
atggaagcat tcccgtcagc taagccttca cttggtgttt tctttgcatc tgttgccccg    1440
cgcttacaac caagatacta ctctatttct tcctcaccca agatggcacc ggataggatt    1500
catgttacat gtgcattagt ctatgagaaa cacctgcag gccgcatcca caaaggagtt    1560
tgttcaactt ggatgaagaa cgcagtgcct atgaccgaga gtcaagattg cagttgggcc    1620
ccaatatacg tccgaacatc caatttcaga ctaccatctg accctaaggt cccggttatc    1680
atgattggac ctggcactgg tttggctcct tttagaggtt tccttcaaga gcggttagct    1740
ttaaaggaag ccggaactga cctcggttta tccattttat tcttcggatg taggaatcgc    1800
aaagtggatt tcatatatga aaacgagctt aacaactttg tggagactgg tgctctttct    1860
gagcttattg ttgctttctc ccgtgaaggc ccgactaagg aatatgtgca acacaagatg    1920
agtgagaagg cttcggatat ctggaacttg ctttctgaag gagcatattt atacgtatgt    1980
ggtgatgcca aaggcatggc caaagatgta catcgaaccc tccacacaat tgtgcaagaa    2040
cagggatctc ttgactcgtc aaaggcagaa ctctacgtga agaatctaca aatgtcagga    2100
agatacctcc gtgacgtttg gtaa                                          2124
```

<210> SEQ ID NO 17
<211> LENGTH: 707
<212> TYPE: PRT
<213> ORGANISM: Stevia rebaudiana

<400> SEQUENCE: 17

```
Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30

Glu Ser Ala Met Leu Pro Thr Ile Ala Met Ile Met Glu Asn Arg Glu
        35                  40                  45

Leu Leu Met Ile Leu Thr Thr Ser Val Ala Val Leu Ile Gly Cys Val
    50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Val Asp
                85                  90                  95

Asp Gly Lys Lys Lys Val Thr Val Phe Phe Gly Thr Gln Thr Gly Thr
                100                 105                 110

Ala Glu Gly Phe Ala Lys Ala Leu Val Glu Glu Ala Lys Ala Arg Tyr
            115                 120                 125

Glu Lys Ala Val Phe Lys Val Ile Asp Leu Asp Asp Tyr Ala Ala Asp
        130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190
```

```
Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
    210                 215                 220

Ala Lys Arg Leu Val Pro Val Gly Leu Gly Asp Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Asp Thr Thr Val Ala Thr Pro Tyr Thr
            260                 265                 270

Ala Ala Val Ala Glu Tyr Arg Val Phe His Glu Lys Pro Asp Ala
        275                 280                 285

Leu Ser Glu Asp Tyr Ser Tyr Thr Asn Gly His Ala Val His Asp Ala
    290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380

Leu Gly Gly Ala Ser Leu Pro Pro Phe Pro Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
        435                 440                 445

Trp Ile Val Ala Ser Gln Arg Ser Leu Leu Glu Val Met Glu Ala Phe
    450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
                485                 490                 495

Pro Asp Arg Ile His Val Thr Cys Ala Leu Val Tyr Glu Lys Thr Pro
            500                 505                 510

Ala Gly Arg Ile His Lys Gly Val Cys Ser Thr Trp Met Lys Asn Ala
        515                 520                 525

Val Pro Met Thr Glu Ser Gln Asp Cys Ser Trp Ala Pro Ile Tyr Val
530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
            580                 585                 590

Leu Phe Phe Gly Cys Arg Asn Arg Lys Val Asp Phe Ile Tyr Glu Asn
        595                 600                 605
```

```
Glu Leu Asn Asn Phe Val Glu Thr Gly Ala Leu Ser Glu Leu Ile Val
    610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655

Leu Tyr Val Cys Gly Asp Ala Lys Gly Met Ala Lys Asp Val His Arg
            660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
    690                 695                 700

Asp Val Trp
705

<210> SEQ ID NO 18
<211> LENGTH: 2133
<212> TYPE: DNA
<213> ORGANISM: Artificial Sequence
<220> FEATURE:
<223> OTHER INFORMATION: Codon optimized

<400> SEQUENCE: 18
atgcaatcag attcagtcaa agtctctcca tttgatttgg tttccgctgc tatgaatggc    60
aaggcaatgg aaaagttgaa cgctagtgaa tctgaagatc aacaacatt gcctgcacta   120 aagatgctag ttgaaaatag agaattgttg acactgttca aacttcctt cgcagttctt   180 attgggtgtc ttgtatttct aatgtggaga cgttcatcct ctaaaaagct ggtacaagat   240
ccagttccac aagttatcgt tgtaaagaag aaagagaagg agtcagaggt tgatgacggg   300
aaaaagaaag tttctatttt ctacggcaca caaacaggaa ctgccgaagg ttttgctaaa   360
gcattagtcg aggaagcaaa agtgagatat gaaaagacct cttttcaaggt tatcgatcta   420 gatgactacg ctgcagatga tgatgaatat gaggaaaaac tgaaaaagga atccttagcc   480
ttcttcttct tggccacata cggtgatggt gaacctactg ataatgctgc taacttctac   540
aagtggttca cagaaggcga cgataaaggt gaatggctga aaaagttaca atacggagta   600
tttggtttag gtaacagaca atatgaacat tcaacaagga tcgctattgt agttgatgat   660
aaacttactg aaatgggagc caaaagatta gtaccagtag gattagggga tgatgatcag   720
tgtatagaag atgacttcac cgcctggaag gaattggtat ggccagaatt ggatcaactt   780
ttaagggacg aagatgatac ttctgtgact accccataca ctgcagccgt attggagtac   840
agagtggttt accatgataa accagcagac tcatatgctg aagatcaaac ccatacaaac   900
ggtcatgttt tcatgatgc acagcatcct tcaagatcta atgtggcttt caaaaaggaa   960
ctacacacct ctcaatcaga taggtcttgt actcacttag aattcgatat ttctcacaca  1020
ggactgtctt acgaaactgg cgatcacgtt ggcgtttatt ccgagaactt gtccgaagtt  1080
gtcgatgaag cactaaaact gttagggtta tcaccagaca catacttctc agtccatgct  1140
gataaggagg atgggacacc tatcggtggt gcttcactac caccacctt tcctccttgc  1200 acattgagag acgctctaac cagatacgca gatgtcttat cctcacctaa aaaggtagct  1260
ttgctggcat tggctgctca tgctagtgat cctagtgaag ccgataggtt aaagttcctg  1320
gcttcaccag ccggaaaaga tgaatatgca caatggatcg tcgccaacca acgttctttg  1380
ctagaagtga tgcaaagttt tccatctgcc aagcctccat taggtgtgtt cttcgcagca  1440
```

```
gtagctccac gtttacaacc aagatactac tctatcagtt catctcctaa gatgtctcct    1500
aacagaatac atgttacatg tgctttggtg tacgagacta ctccagcagg cagaattcac    1560
agaggattgt gttcaacctg atgaaaaat gctgtcccett taacagagtc acctgattgc    1620
```

```
gtagctccac gtttacaacc aagatactac tctatcagtt catctcctaa gatgtctcct    1500
aacagaatac atgttacatg tgctttggtg tacgagacta ctccagcagg cagaattcac    1560
agaggattgt gttcaacctg atgaaaaat  gctgtcccett taacagagtc acctgattgc    1620
tctcaagcat ccattttcgt tagaacatca aatttcagac ttccagtgga tccaaaagtt    1680
ccagtcatta tgataggacc aggcactggt cttgccccat caggggcttt cttcaagag     1740 agattggcct tgaaggaatc tggtacagaa ttgggttctt ctatcttttt ctttggttgc    1800
cgtaatagaa aagttgactt tatctacgag gacgagctta acaattttgt tgagacagga    1860
gcattgtcag aattgatcgt cgcattttca agagaaggga ctgccaaaga gtacgttcag    1920
cacaagatga gtcaaaaagc ctccgatata tggaaacttc aagtgaagg tgcctatctt     1980 tatgtctgtg gcgatgcaaa gggcatggcc aaggatgtcc atagaactct gcatacaatt    2040
gttcaggaac aagggagtct ggattcttcc aaggctgaat tgtacgtcaa aaacttacag    2100
atgtctggaa gatacttaag agatgtttgg taa                                 2133
```

<210> SEQ ID NO 19
<211> LENGTH: 710
<212> TYPE: PRT
<213> ORGANISM: Stevia rebaudiana

<400> SEQUENCE: 19

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Lys Lys Glu Lys Ser Glu
                85                  90                  95

Val Asp Asp Gly Lys Lys Lys Val Ser Ile Phe Tyr Gly Thr Gln Thr
            100                 105                 110

Gly Thr Ala Glu Gly Phe Ala Lys Ala Leu Val Glu Glu Ala Lys Val
        115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Lys Leu Thr Glu
    210                 215                 220

Met Gly Ala Lys Arg Leu Val Pro Val Gly Leu Gly Asp Asp Gln
225                 230                 235                 240

Cys Ile Glu Asp Asp Phe Thr Ala Trp Lys Glu Leu Val Trp Pro Glu
                245                 250                 255
```

```
Leu Asp Gln Leu Leu Arg Asp Glu Asp Thr Ser Val Thr Thr Pro
            260                 265                 270

Tyr Thr Ala Ala Val Leu Glu Tyr Arg Val Val Tyr His Asp Lys Pro
            275                 280                 285

Ala Asp Ser Tyr Ala Glu Asp Gln Thr His Thr Asn Gly His Val Val
290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
            355                 360                 365

Gly Leu Ser Pro Asp Thr Tyr Phe Ser Val His Ala Asp Lys Glu Asp
370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
            435                 440                 445

Tyr Ala Gln Trp Ile Val Ala Asn Gln Arg Ser Leu Leu Glu Val Met
450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
            515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Phe Gly Cys Arg Asn Arg Lys Val Asp Phe Ile
            595                 600                 605

Tyr Glu Asp Glu Leu Asn Asn Phe Val Glu Thr Gly Ala Leu Ser Glu
610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670
```

Val His Arg Thr Leu His Thr Ile Val Gln Glu Gln Gly Ser Leu Asp
            675                 680                 685

Ser Ser Lys Ala Glu Leu Tyr Val Lys Asn Leu Gln Met Ser Gly Arg
        690                 695                 700

Tyr Leu Arg Asp Val Trp
705                 710

<210> SEQ ID NO 20
<211> LENGTH: 511
<212> TYPE: PRT
<213> ORGANISM: Rubus suavissimus

<400> SEQUENCE: 20

Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
                20                  25                  30

Ser Phe Phe Ser Asn Lys Ser Ala Gln Ala Lys Leu Pro Pro Val Pro
            35                  40                  45

Val Val Pro Gly Leu Pro Val Ile Gly Asn Leu Leu Gln Leu Lys Glu
        50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
                85                  90                  95

Thr Gln Val Ala Lys Glu Ala Met Val Thr Arg Tyr Leu Ser Ile Ser
            100                 105                 110

Thr Arg Lys Leu Ser Asn Ala Leu Lys Ile Leu Thr Ala Asp Lys Cys
        115                 120                 125

Met Val Ala Ile Ser Asp Tyr Asn Asp Phe His Lys Met Ile Lys Arg
130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Glu Leu Gly Thr Thr Leu Ser Arg
210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

```
Ala Lys Asp Ser Lys Arg Gln Asp Arg Leu Tyr Gln Glu Ile Gln Lys
                340                 345                 350

Val Cys Gly Ser Glu Met Val Thr Glu Glu Tyr Leu Ser Gln Leu Pro
                355                 360                 365

Tyr Leu Asn Ala Val Phe His Glu Thr Leu Arg Lys His Ser Pro Ala
    370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
                420                 425                 430

Arg Phe Leu Asp Pro Lys Phe Asp Pro Met Asp Leu Tyr Lys Thr Met
                435                 440                 445

Ala Phe Gly Ala Gly Lys Arg Val Cys Ala Gly Ser Leu Gln Ala Met
    450                 455                 460

Leu Ile Ala Cys Pro Thr Ile Gly Arg Leu Val Gln Glu Phe Glu Trp
465                 470                 475                 480

Lys Leu Arg Asp Gly Glu Glu Glu Asn Val Asp Thr Val Gly Leu Thr
                485                 490                 495

Thr His Lys Arg Tyr Pro Met His Ala Ile Leu Lys Pro Arg Ser
                500                 505                 510

<210> SEQ ID NO 21
<211> LENGTH: 523
<212> TYPE: PRT
<213> ORGANISM: Rubus suavissimus

<400> SEQUENCE: 21

Met Glu Val Thr Val Ala Ser Ser Val Ala Leu Ser Leu Val Phe Ile
1               5                   10                  15

Ser Ile Val Val Arg Trp Ala Trp Ser Val Asn Trp Val Trp Phe
                20                  25                  30

Lys Pro Lys Lys Leu Glu Arg Phe Leu Arg Glu Gln Gly Leu Lys Gly
                35                  40                  45

Asn Ser Tyr Arg Phe Leu Tyr Gly Asp Met Lys Glu Asn Ser Ile Leu
    50                  55                  60

Leu Lys Gln Ala Arg Ser Lys Pro Met Asn Leu Ser Thr Ser His Asp
65                  70                  75                  80

Ile Ala Pro Gln Val Thr Pro Phe Val Asp Gln Thr Val Lys Ala Tyr
                85                  90                  95

Gly Lys Asn Ser Phe Asn Trp Val Gly Pro Ile Pro Arg Val Asn Ile
                100                 105                 110

Met Asn Pro Glu Asp Leu Lys Asp Val Leu Thr Lys Asn Val Asp Phe
            115                 120                 125

Val Lys Pro Ile Ser Asn Pro Leu Ile Lys Leu Leu Ala Thr Gly Ile
        130                 135                 140

Ala Ile Tyr Glu Gly Glu Lys Trp Thr Lys His Arg Arg Ile Ile Asn
145                 150                 155                 160

Pro Thr Phe His Ser Glu Arg Leu Lys Arg Met Leu Pro Ser Phe His
                165                 170                 175

Gln Ser Cys Asn Glu Met Val Lys Glu Trp Glu Ser Leu Val Ser Lys
                180                 185                 190

Glu Gly Ser Ser Cys Glu Leu Asp Val Trp Pro Phe Leu Glu Asn Met
```

```
                    195                 200                 205
Ser Ala Asp Val Ile Ser Arg Thr Ala Phe Gly Thr Ser Tyr Lys Lys
210                 215                 220

Gly Gln Lys Ile Phe Glu Leu Leu Arg Glu Gln Val Ile Tyr Val Thr
225                 230                 235                 240

Lys Gly Phe Gln Ser Phe Tyr Ile Pro Gly Trp Arg Phe Leu Pro Thr
                    245                 250                 255

Lys Met Asn Lys Arg Met Asn Glu Ile Asn Glu Glu Ile Lys Gly Leu
                260                 265                 270

Ile Arg Gly Ile Ile Ile Asp Arg Glu Gln Ile Ile Lys Ala Gly Glu
            275                 280                 285

Glu Thr Asn Asp Asp Leu Leu Gly Ala Leu Met Glu Ser Asn Leu Lys
        290                 295                 300

Asp Ile Arg Glu His Gly Lys Asn Asn Lys Asn Val Gly Met Ser Ile
305                 310                 315                 320

Glu Asp Val Ile Gln Glu Cys Lys Leu Phe Tyr Phe Ala Gly Gln Glu
                    325                 330                 335

Thr Thr Ser Val Leu Leu Ala Trp Thr Met Val Leu Leu Gly Gln Asn
                340                 345                 350

Gln Asn Trp Gln Asp Arg Ala Arg Gln Glu Val Leu Gln Val Phe Gly
            355                 360                 365

Ser Ser Lys Pro Asp Phe Asp Gly Leu Ala His Leu Lys Val Val Thr
        370                 375                 380

Met Ile Leu Leu Glu Val Leu Arg Leu Tyr Pro Pro Val Ile Glu Leu
385                 390                 395                 400

Ile Arg Thr Ile His Lys Lys Thr Gln Leu Gly Lys Leu Ser Leu Pro
                    405                 410                 415

Glu Gly Val Glu Val Arg Leu Pro Thr Leu Leu Ile His His Asp Lys
                420                 425                 430

Glu Leu Trp Gly Asp Asp Ala Asn Gln Phe Asn Pro Glu Arg Phe Ser
            435                 440                 445

Glu Gly Val Ser Lys Ala Thr Lys Asn Arg Leu Ser Phe Phe Pro Phe
        450                 455                 460

Gly Ala Gly Pro Arg Ile Cys Ile Gly Gln Asn Phe Ser Met Met Glu
465                 470                 475                 480

Ala Lys Leu Ala Leu Ala Leu Ile Leu Gln His Phe Thr Phe Glu Leu
                    485                 490                 495

Ser Pro Ser His Ala His Ala Pro Ser His Arg Ile Thr Leu Gln Pro
                500                 505                 510

Gln Tyr Gly Val Arg Ile Ile Leu His Arg Arg
            515                 520
```

<210> SEQ ID NO 22
<211> LENGTH: 701
<212> TYPE: PRT
<213> ORGANISM: Siraitia grosvenorii

<400> SEQUENCE: 22

```
Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
                20                  25                  30

Val Ile Phe Glu Asn Arg Glu Leu Val Ala Ile Leu Thr Thr Ser Ile
            35                  40                  45
```

```
Ala Val Met Ile Gly Cys Phe Val Val Leu Met Trp Arg Arg Ala Gly
 50                  55                  60

Ser Arg Lys Val Lys Asn Val Glu Leu Pro Lys Pro Leu Ile Val His
 65                  70                  75                  80

Glu Pro Glu Pro Glu Val Glu Asp Gly Lys Lys Lys Val Ser Ile Phe
                     85                  90                  95

Phe Gly Thr Gln Thr Gly Thr Ala Glu Gly Phe Ala Lys Ala Leu Ala
                100                 105                 110

Asp Glu Ala Lys Ala Arg Tyr Glu Lys Ala Thr Phe Arg Val Val Asp
                115                 120                 125

Leu Asp Asp Tyr Ala Ala Asp Asp Gln Tyr Glu Glu Lys Leu Lys
130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
                180                 185                 190

Gly Asn Arg Gln Tyr Glu His Phe Asn Lys Ile Ala Lys Val Ala Asp
                195                 200                 205

Glu Leu Leu Glu Ala Gln Gly Gly Asn Arg Leu Val Lys Val Gly Leu
                210                 215                 220

Gly Asp Asp Asp Gln Cys Ile Glu Asp Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
                260                 265                 270

Val Phe His Asp Ser Ala Asp Val Ala Ala Glu Asp Lys Ser Trp Ile
                275                 280                 285

Asn Ala Asn Gly His Ala Val His Asp Ala Gln His Pro Phe Arg Ser
290                 295                 300

Asn Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
                340                 345                 350

Asp Glu Ala Leu Asn Leu Leu Gly Leu Ser Pro Glu Thr Tyr Phe Ser
                355                 360                 365

Ile Tyr Thr Asp Asn Glu Asp Gly Thr Pro Leu Gly Gly Ser Ser Leu
370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

Ala His Ala Ser Asn Pro Val Glu Ala Asp Arg Leu Arg Tyr Leu Ala
                420                 425                 430

Ser Pro Ala Gly Lys Asp Glu Tyr Ala Gln Ser Val Ile Gly Ser Gln
                435                 440                 445

Lys Ser Leu Leu Glu Val Met Ala Glu Phe Pro Ser Ala Lys Pro Pro
450                 455                 460

Leu Gly Val Phe Phe Ala Ala Val Ala Pro Arg Leu Gln Pro Arg Phe
```

-continued

```
            465                 470                 475                 480

Tyr Ser Ile Ser Ser Ser Pro Arg Met Ala Pro Ser Arg Ile His Val
                    485                 490                 495

Thr Cys Ala Leu Val Tyr Asp Lys Met Pro Thr Gly Arg Ile His Lys
                500                 505                 510

Gly Val Cys Ser Thr Trp Met Lys Asn Ser Val Pro Met Glu Lys Ser
            515                 520                 525

His Glu Cys Ser Trp Ala Pro Ile Phe Val Arg Gln Ser Asn Phe Lys
        530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
                565                 570                 575

Glu Ser Gly Val Glu Leu Gly Pro Ser Ile Leu Phe Phe Gly Cys Arg
                580                 585                 590

Asn Arg Arg Met Asp Tyr Ile Tyr Glu Asp Glu Leu Asn Asn Phe Val
                595                 600                 605

Glu Thr Gly Ala Leu Ser Glu Leu Val Ile Ala Phe Ser Arg Glu Gly
        610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
                645                 650                 655

Ala Lys Gly Met Ala Lys Asp Val His Arg Thr Leu His Thr Ile Met
                660                 665                 670

Gln Glu Gln Gly Ser Leu Asp Ser Ser Lys Ala Glu Ser Met Val Lys
            675                 680                 685

Asn Leu Gln Met Asn Gly Arg Tyr Leu Arg Asp Val Trp
        690                 695                 700
```